(12) United States Patent  
Coppeta et al.

(10) Patent No.: US 7,534,241 B2
(45) Date of Patent: May 19, 2009

(54) MICRO-RESERVOIR OSMOTIC RELEASE SYSTEMS AND MICROTUBE ARRAY DEVICE

(75) Inventors: Jonathan R. Coppeta, Windham, NH (US); John T. Santini, Jr., North Chelmsford, MA (US); Scott A. Uhland, Roslindale, MA (US)

(73) Assignee: MicroCHIPS, Inc., Bedford, MA (US)

( * ) Notice: Subject to any disclaimer, the term of this patent is extended or adjusted under 35 U.S.C. 154(b) by 959 days.

(21) Appl. No.: 10/668,573

(22) Filed: Sep. 23, 2003

(65) Prior Publication Data

US 2004/0106914 A1 Jun. 3, 2004

Related U.S. Application Data

(60) Provisional application No. 60/412,746, filed on Sep. 23, 2002.

(51) Int. Cl.
*A61K 9/22* (2006.01)
(52) U.S. Cl. .................................. 604/891.1
(58) Field of Classification Search ... 604/890.1–892.1, 604/93.01, 173
See application file for complete search history.

(56) References Cited

U.S. PATENT DOCUMENTS

| | | | |
|---|---|---|---|
| 3,692,027 A | | 9/1972 | Ellinwood, Jr. |
| 3,762,540 A | * | 10/1973 | Baumann et al. ............ 206/219 |
| 3,952,741 A | | 4/1976 | Baker |
| 4,003,379 A | | 1/1977 | Ellinwood, Jr. |
| 4,111,202 A | * | 9/1978 | Theeuwes ................ 604/892.1 |
| 4,146,029 A | | 3/1979 | Ellinwood, Jr. |
| 4,312,347 A | * | 1/1982 | Magoon et al. .......... 604/891.1 |

(Continued)

FOREIGN PATENT DOCUMENTS

DE 29 11 558 A1 9/1980

(Continued)

OTHER PUBLICATIONS

Bae, et al., "Pulsatile Drug Release by Electric Stimulus," ACS Symp. Series *Polymeric Drugs & Drug Admin.*, pp. 99-110 (1994).

(Continued)

*Primary Examiner*—Kevin C Sirmons
*Assistant Examiner*—Elizabeth R MacNeill
(74) *Attorney, Agent, or Firm*—Sutherland Asbill & Brennan LLP

(57) ABSTRACT

Devices and methods are provided for controlled release of chemical molecules, such as drugs. One device comprises a plurality of reservoirs; a rupturable covering, such as a thin metal film, enclosing a first end of each reservoir; a release formulation in each reservoir comprising chemical molecules for release; an expanding material layer in each reservoir; and a semi-permeable membrane enclosing a second end of each reservoir distal the release formulation, the semi-permeable membrane being operable to permit selected molecules (e.g., water) from outside the reservoir to diffuse to the expanding material layer to expand the expanding material layer and displace the release formulation in an amount effective rupture the rupturable membrane and discharge the release formulation. The device may further comprises a reservoir cap covering semi-permeable membrane and means for selectively disintegrating the reservoir cap to initiate diffusion of fluid molecules from outside the reservoir and through the semi-permeable membrane.

27 Claims, 11 Drawing Sheets

U.S. PATENT DOCUMENTS

| | | | |
|---|---|---|---|
| 4,360,019 A | | 11/1982 | Portner et al. |
| 4,425,117 A | * | 1/1984 | Hugemann et al. ......... 604/244 |
| 4,507,115 A | | 3/1985 | Kambara et al. |
| 4,585,652 A | | 4/1986 | Miller et al. |
| 4,595,583 A | * | 6/1986 | Eckenhoff et al. ......... 424/438 |
| 4,731,049 A | | 3/1988 | Parsi |
| 4,781,714 A | | 11/1988 | Eckenhoff et al. |
| 4,874,388 A | | 10/1989 | Wong et al. |
| 4,950,258 A | * | 8/1990 | Kawai et al. ............... 604/530 |
| 4,957,494 A | | 9/1990 | Wong et al. |
| 5,041,107 A | | 8/1991 | Heil, Jr. |
| 5,042,975 A | | 8/1991 | Chien et al. |
| 5,122,128 A | * | 6/1992 | Cardinal et al. ......... 604/890.1 |
| 5,167,625 A | | 12/1992 | Jacobsen et al. |
| 5,196,002 A | | 3/1993 | Hanover et al. |
| 5,252,294 A | | 10/1993 | Kroy et al. |
| 5,254,081 A | | 10/1993 | Maurer et al. |
| 5,279,607 A | | 1/1994 | Schentag et al. |
| 5,318,557 A | | 6/1994 | Gross |
| 5,366,454 A | | 11/1994 | Currie et al. |
| 5,368,588 A | | 11/1994 | Bettinger |
| 5,368,704 A | | 11/1994 | Madou et al. |
| 5,401,110 A | * | 3/1995 | Neeley ...................... 400/621 |
| 5,427,585 A | | 6/1995 | Bettinger |
| 5,429,822 A | | 7/1995 | Gresser et al. |
| 5,443,508 A | | 8/1995 | Giampapa |
| 5,474,527 A | | 12/1995 | Bettinger |
| 5,499,979 A | | 3/1996 | Wong et al. |
| 5,533,995 A | | 7/1996 | Corish et al. |
| 5,574,313 A | | 11/1996 | McKleroy |
| 5,660,846 A | | 8/1997 | Cheikh |
| 5,797,898 A | * | 8/1998 | Santini et al. ............ 604/890.1 |
| 5,824,204 A | | 10/1998 | Jerman |
| 5,843,767 A | | 12/1998 | Beattie |
| 5,911,737 A | * | 6/1999 | Lee et al. ..................... 606/209 |
| 5,976,101 A | | 11/1999 | Sibalis |
| 6,062,461 A | | 5/2000 | Sparks et al. |
| 6,083,763 A | | 7/2000 | Balch |
| 6,112,116 A | | 8/2000 | Fischell et al. |
| 6,114,658 A | | 9/2000 | Roth et al. |
| 6,123,861 A | | 9/2000 | Santini, Jr. et al. |
| 6,140,740 A | | 10/2000 | Porat et al. |
| 6,171,850 B1 | | 1/2001 | Nagle et al. |
| 6,183,466 B1 | * | 2/2001 | Wong et al. ............... 604/892.1 |
| 6,200,293 B1 | * | 3/2001 | Kriesel et al. ............... 604/132 |
| 6,261,584 B1 | | 7/2001 | Peery et al. |
| 6,334,859 B1 | | 1/2002 | Richter |
| 6,349,232 B1 | | 2/2002 | Gordon |
| 6,491,666 B1 | | 12/2002 | Santini, Jr. et al. |
| 6,527,762 B1 | | 3/2003 | Santini, Jr. et al. |
| 6,537,250 B1 | | 3/2003 | Kriesel |
| 6,537,256 B2 | | 3/2003 | Santini, Jr. et al. |
| 6,551,838 B2 | | 4/2003 | Santini, Jr. et al. |
| 6,656,162 B2 | | 12/2003 | Santini, Jr. et al. |
| 6,663,615 B1 | | 12/2003 | Madou et al. |
| 6,669,683 B2 | | 12/2003 | Santini, Jr. et al. |
| 6,692,456 B1 | * | 2/2004 | Eppstein et al. .............. 604/22 |
| 6,726,678 B1 | | 4/2004 | Nelson et al. |
| 6,849,463 B2 | * | 2/2005 | Santin et al. ................ 436/518 |
| 7,025,323 B2 | * | 4/2006 | Krulevitch et al. ............ 251/11 |
| 7,041,130 B2 | * | 5/2006 | Santini et al. .............. 623/1.42 |
| 7,052,488 B2 | * | 5/2006 | Uhland ................... 604/891.1 |
| 2002/0072784 A1 | | 6/2002 | Sheppard, Jr. et al. |
| 2002/0099359 A1 | | 7/2002 | Santini, Jr. et al. |
| 2002/0107470 A1 | | 8/2002 | Richards et al. |
| 2002/0138067 A1 | | 9/2002 | Sheppard, Jr. et al. |
| 2002/0151776 A1 | | 10/2002 | Shawgo et al. |
| 2002/0183721 A1 | | 12/2002 | Santini, Jr. et al. |
| 2002/0187260 A1 | | 12/2002 | Sheppard, Jr. et al. |
| 2003/0010808 A1 | | 1/2003 | Uhland et al. |
| 2003/0104590 A1 | | 6/2003 | Santini, Jr. et al. |
| 2003/0105455 A1 | | 6/2003 | Santini, Jr. et al. |
| 2003/0135201 A1 | * | 7/2003 | Gonnelli ................. 604/890.1 |

FOREIGN PATENT DOCUMENTS

| DE | 197 16 683 C1 | 6/1998 |
|---|---|---|
| WO | WO 93/03790 A1 | 3/1993 |
| WO | WO 02/056862 A2 | 7/2002 |

OTHER PUBLICATIONS

Haroun, et al., "Local Drug Delivery," *Curr. Opin. Oncol.* 12(3): 187-93 (2000) (abstract only).

Jackman, et al., "Fabricating Large Arrays of Microwells with Arbitrary Dimensions and Filling them Using Discontinuous Dewetting," *Anal. Chem.* 70: 2280-87 (1998).

Santini, et al., "Microchips as Controlled Drug-Delivery Devices," *Angew Chem. Int. Ed. Engl.* 39(14): 2396-407 (2000).

Santini, et al., "Microchip Technology in Drug Delivery," *Ann. Med.* 32(6) 377-79 (2001).

Santini, et al., "A Controlled-Release Microchip," *Nature* 397(6717): 335-38 (1999).

Tao, et al., Microfabricated Drug Delivery Systems: From Particles to Pores:, *Adv. Drug Deliv. Res.* 55(3): 315-28 (2003).

* cited by examiner

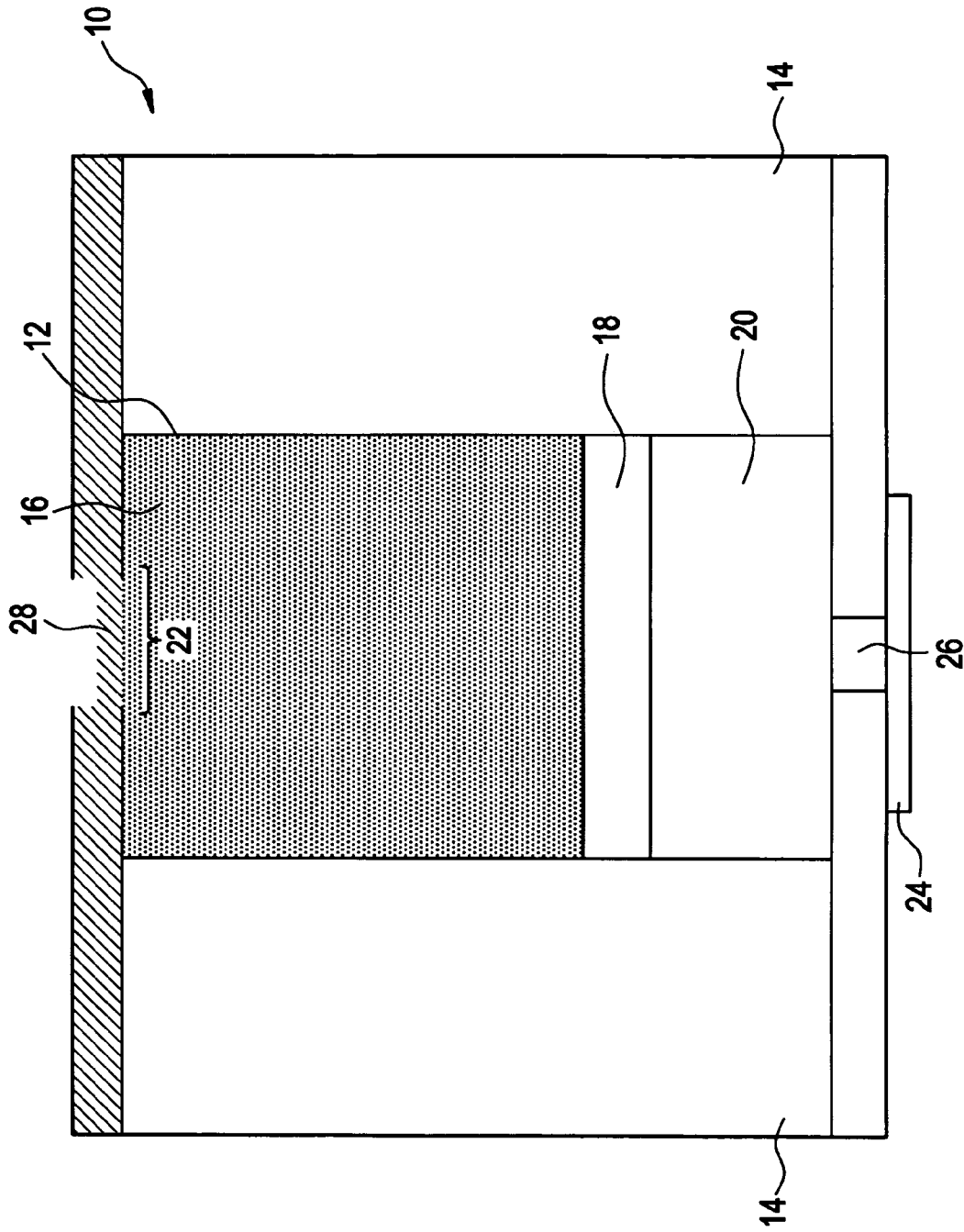

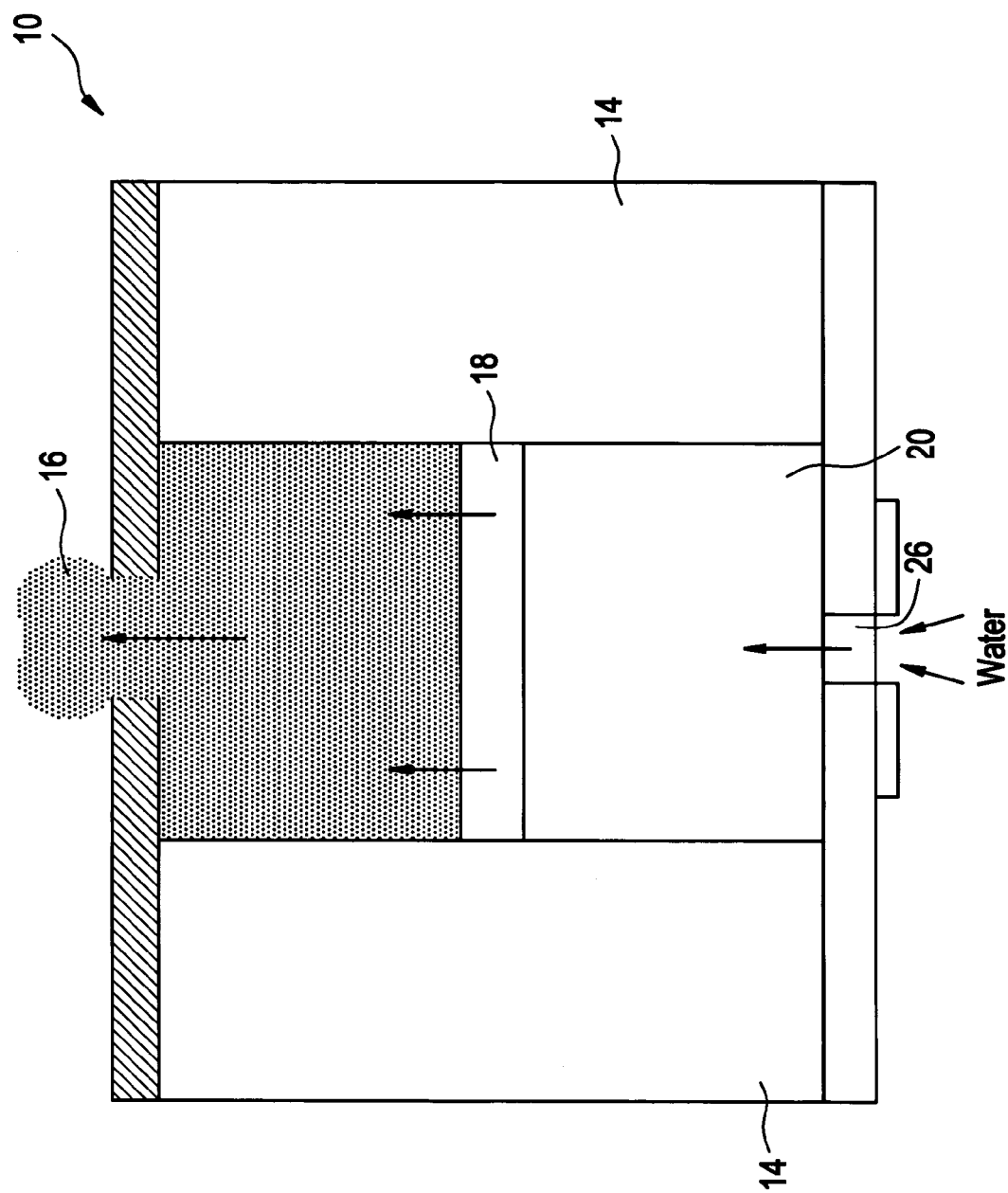

MICRO-RESERVOIR OSMOTIC RELEASE SYSTEMS AND MICROTUBE ARRAY DEVICE

CROSS-REFERENCE TO RELATED APPLICATIONS

Priority is claimed to U.S. Provisional Application No. 60/412,746, filed Sep. 23, 2002. The application is incorporated herein by reference.

BACKGROUND OF THE INVENTION

This invention relates to devices and methods for the controlled release of small quantities of drugs and other molecules from reservoirs, the controlled exposure of microsized secondary devices located in reservoirs, or combinations thereof.

U.S. Pat. No. 5,797,898, No. 6,123,861, No. 6,527,762, No. 6,491,666, and No. 6,551,838 disclose devices having an array of multiple, discrete reservoirs which contain small quantities of drugs or other molecules or secondary devices for controlled release. For example, the device can be implanted for the controlled administration of drug to a patient in need thereof. Various release mechanisms are described. In one embodiment, each reservoir has a reservoir cap positioned on the reservoir over the molecules, so that the molecules are released from the device by diffusion through or upon disintegration of the reservoir cap. The reservoir caps can be controllably disintegrated to release the molecules from the reservoirs at selected times. In one embodiment, which is disclosed in U.S. Pat. No. 5,797,898, the reservoir cap is a metal film, which functions as an anode, and an electric potential is applied between the anode and a cathode to cause the metal film to oxidize and disintegrate. It would be advantageous to provide additional mechanisms for releasing the drug molecules from the reservoirs, particularly active release mechanisms that can provide an enhanced rate of release of the molecules from the reservoirs, thereby speeding the rate the released molecules diffuse into the target fluid, e.g., at the site of implantation of the device.

U.S. Pat. No. 6,123,861 discloses microchip reservoir devices made using a process that requires several steps including a series of MEMS processing steps. It would be desirable to provide new types of reservoir array devices and methods of manufacture therefor, particularly where simplified methods can be used to produce a complete and hermetically sealed micro-reservoir.

SUMMARY OF THE INVENTION

Devices and methods are provided for the controlled release of chemical molecules. In one aspect, the device comprises a plurality of reservoirs; a rupturable covering (e.g., a thin metal film) enclosing a first end of each reservoir; a release formulation positioned in each reservoir and comprising the chemical molecules for release; an expanding material layer positioned in each reservoir; and a semi-permeable membrane enclosing a second end of each reservoir distal the release formulation, the semi-permeable membrane being operable to permit selected molecules from outside the reservoir to diffuse to the expanding material layer to cause the expanding material layer to expand and displace the release formulation in an amount effective rupture the rupturable membrane and discharge the release formulation from the reservoir. In one embodiment, the device further comprises a reservoir cap covering semi-permeable membrane and a means for selectively disintegrating the reservoir cap to initiate molecular diffusion of fluid molecules from outside the reservoir and through the semi-permeable membrane.

In various embodiments, the reservoirs are disposed in a substrate, or each reservoir is disposed in a microtube such that the device comprises an array of microtubes. In one embodiment, the release formulation is a drug formulation.

In one embodiment, the device further includes a movable piston in each reservoir between the release formulation and the expanding material, wherein expansion of the expanding material layer drives the piston to displace the release formulation. Alternatively or additionally, the device can further include a collapsible container which separates the release formulation and the expanding material layer, wherein expansion of the expanding material layer collapses the collapsible container to displace the release formulation.

In one embodiment, the expanding material layer comprises an osmotic agent. In one embodiment, the reservoirs are defined within sidewalls and the expanding material layer is disposed between the sidewalls and the release formulation.

In another aspect, a device is provided for the controlled release of a fluid drug formulation. In one embodiment, the device comprises a first reservoir comprising a fluid drug formulation; a second reservoir comprising an inert fluid, the first reservoir and the second reservoir each having a discharge outlet controlled by a shared flow switch, the flow switch being configured to discharge either the drug formulation or the inert fluid from the device; and an osmotic engine for driving the fluid drug formulation from the first reservoir and the inert fluid from the second reservoir.

In one embodiment, the osmotic engine comprises (i) a first piston which drives the fluid drug formulation from the first reservoir and (ii) a second piston which drives the inert fluid from the second reservoir. In another embodiment, the osmotic engine comprises a body containing an osmotic agent covered by an impermeable shell except for an area comprising a semi-permeable membrane.

In another aspect, a device is provided for the controlled release of chemical molecules, which device comprises an array of microtubes, each microtube comprising a reservoir defined therein; a release formulation which comprises the chemical molecules, the release formulation being disposed in each reservoir; a rupturable covering enclosing a first end of each reservoir; and a means for rupturing the rupturable covering and positively displacing the release formulation through an opening at the first end, to release the chemical molecules. The rupturable covering can be provided with one or more defects to facilitate rupture.

In one embodiment, the means for rupturing comprises a layer of an expanding material, and the release formulation is disposed between the layer of expanding material and the rupturable covering. A layer of a barrier material can be disposed between the release formulation and the expanding material, in one embodiment.

In another embodiment, the expanding material can be activated to expand upon application of heat. For example, the means for rupturing can comprise a resistive heating element or resistive coating for heating the end of the microtube distal the rupturable covering upon application of an electric current through the resistive heating element or resistive coating. In another example, the means for rupturing comprises a reactive coating over at least a portion of the end of the microtube distal the rupturable covering.

In one embodiment, at least a portion of the microtube is constructed of a shape memory alloy. In another embodiment, the release formulation is contained in a rigid substructure within the reservoir.

In one embodiment, the release formulation is a drug formulation. In one embodiment, the rupturable covering comprises a metal foil.

In one embodiment, the microtubes are connected by and extend from a planar base. The microtubes and the planar base can be constructed of a biocompatible metal, such as titanium, gold, platinum, Nitinol, or stainless steel. In one embodiment, the microtubes are fused to the planar base by an electroplating process, an electroless plating process, or by a brazing process. In another embodiment, the planar base is joined to a metal package, which together enclose control electronics for controlling the means for rupturing.

In another aspect, a method is provided for the controlled delivery of chemical molecules. The method includes placing any of the aforementioned devices at a site for release of the chemical molecules, and then initiating expansion of the expanding material to rupture the rupturable covering and release the chemical molecules at the site. In exemplary embodiments, the chemical molecules comprise a drug and the site is in vivo.

In one specific embodiment, the method is for the controlled delivery of a drug formulation, comprising placing the aforementioned osmotic engine device at a site for release of the drug formulation, and activating the osmotic engine to drive the fluid drug formulation from the first reservoir. The method may further include switching the flow switch to stop the flow of fluid drug formulation from the first reservoir and to start the flow of inert fluid from the second reservoir, and then switching the flow switch again to stop the flow of inert fluid from the second reservoir and restart the flow of fluid drug formulation from the first reservoir.

BRIEF DESCRIPTION OF THE DRAWINGS

FIG. 1A is a cross-sectional view of one embodiment of a reservoir of device which uses an osmotic pressure mechanism to drive the release of molecules out of the reservoir. FIG. 1B is a cross-section view of the device of FIG. 1A in the process of releasing molecules following reservoir cap rupture.

DETAILED DESCRIPTION OF THE INVENTION

Figure 2:
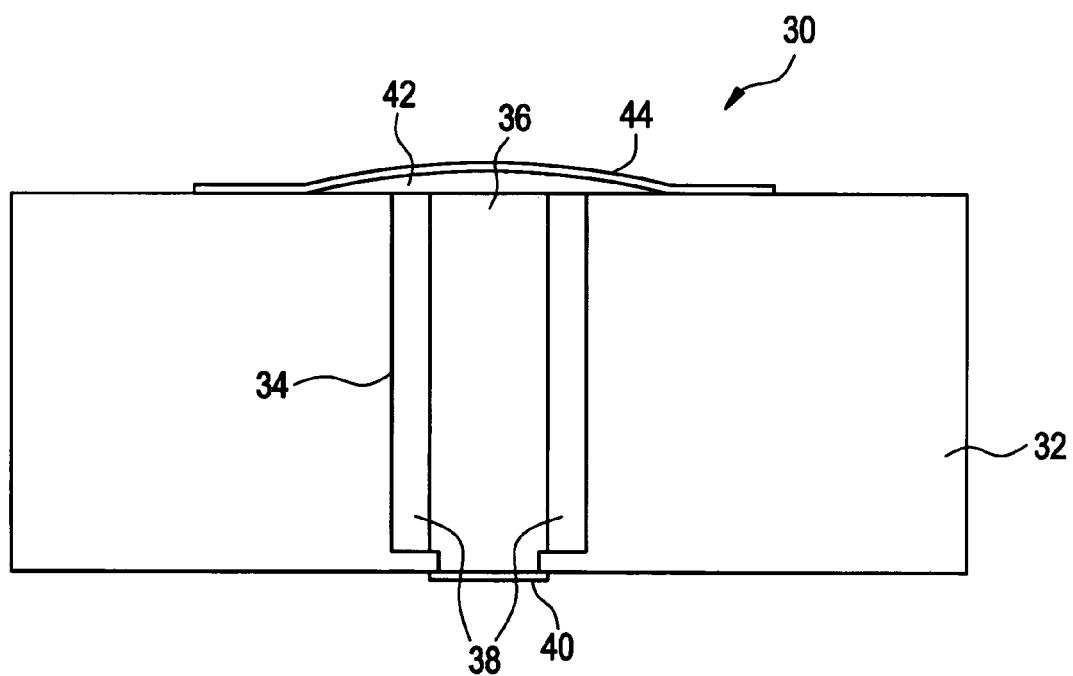
FIG. 2 is a cross-sectional view of another embodiment of a reservoir of device which uses an osmotic pressure mechanism to squeeze the molecules out of the reservoir.

Improved devices, systems, and methods have been developed for the controlled release of chemicals, such as drug formulations. Advantageously, several of the embodiments utilize positive displacement techniques to facilitate release, accelerating the release rate beyond that which would occur if release depended solely on passive mass diffusion to move the chemical from the reservoirs. The devices and methods described herein can provide very fast release of drug or other reservoir contents, which may be useful, for example, in releasing drugs whose efficacy is dependent on a fast pharmacokinetic pulsatile profile.

As used herein, the terms "accelerated release" and "accelerating the release" refer to an increase in the transport rate of drug out of the reservoir relative to the transport rate of the drug solely by diffusion down its own chemical gradient. The terms also refer to expelling reservoir contents that would not otherwise egress from an open reservoir, i.e., where no or negligible diffusion could occur.

As used herein, the terms "comprise," "comprising," "include," and "including" are intended to be open, non-limiting terms, unless the contrary is expressly indicated.

The Reservoir Device and System for Releasing Molecules

In one embodiment, the positive displacement mechanism utilizes an osmotic pressure generating material or other swellable material. In one embodiment, initiation of pressure generation is controlled by a reservoir cap actuation mechanism. Multiple dosing can be achieved by the use of multiple reservoirs within the device, each being separately actuable to initiate molecule release when desired. For example, the device could include an array of tens or hundreds of reservoirs, to store and deliver tens or hundreds of doses of drug. In another embodiment, multiple drug doses are stored in a single reservoir and a switching valve is used to stop/start the flow of drug molecules from the reservoir. Initiation of release of the molecules can be controlled by passive means, active means, or a combination thereof. Once initiated, the drug molecules are actively expelled from the reservoir(s). The delivery device can be fabricated in a variety of ways and configurations to control the drug release kinetics.

In another aspect, microtube devices are provided. Each device comprises an array of microtubes, each of which comprises a reservoir containing molecules for storage and controlled release.

Osmotic Release Systems

In one embodiment, the device relies upon an osmotic pressure generating mechanism to control release of the reservoir contents from a reservoir in a substrate or in microtube. For example, in one embodiment, each of the micro-reservoirs can be described, for purposes of illustration, as functioning like a DUROS™ pump. See, e.g., http://www.alzet.com/products/productsrates.html and U.S. Pat. No. 6,270,787 to Ayer, which is expressly incorporated herein by reference.

One embodiment of such a drug delivery device is illustrated in FIGS. 1A-B. FIG. 1A shows a portion of a device 10, which includes a reservoir 12 in a substrate 14. While only one reservoir is shown, the device includes two or more reservoirs, and preferably tens or hundreds or more identical reservoirs, in an array in the substrate. The reservoir 12 contains a drug formulation 16 for release. The drug formulation is adjacent the release opening 22. A piston 18 is also provided in the reservoir. The piston 18 separates the drug formulation 16 from an osmotic pressure generating agent 20. In an alternative embodiment, another suitable swellable material, e.g., a water-swellable or other fluid-swellable material, can be used in place of the osmotic pressure generating agent. As the osmotic pressure generating agent 20 swells, pressure is generated to drive the piston 18 against the drug formulation 16. Consequently, the drug formulation 16 is pushed out of the reservoir 12, as illustrated in FIG. 1B. The swelling of osmotic pressure generating agent 20 occurs when fluid enters through semi-permeable membrane 26. When activated, this membrane 26 allows transport of water (or another fluid, e.g., a physiological fluid) from outside the device 10 and through the membrane 26 at a pre-determined rate, causing the osmotic pressure generating agent 20 to swell and drive the piston 18. The water, however, cannot/does not contact the membrane 26, and thus traverse it, while the membrane 26 is covered by a fluid impermeable reservoir cap 24. Reservoir cap 24 controls activation of release, i.e., the time at which water transport is initiated. That is, the water is unable to contact the osmotic pressure generating agent 20 until the impermeable reservoir cap 24 is ruptured, disintegrated, or otherwise made permeable, to permit water/fluid to pass through the semi-permeable membrane 26. The pressure of the drug formulation 16 on the rupturable covering 28 covering the release opening 22 causes the rupturable covering 28 to rupture, allowing the drug formulation to be move from the reservoir and into surrounding environment (e.g., into the body of a patient).

To initiate swelling, the reservoir cap 24 can be ruptured or disintegrated by any of several active or passive means, such as described in U.S. patent application Ser. No. 10/641,507, filed Aug. 15, 2003, or in U.S. Pat. No. 5,797,898, No. 6,123,861, No. 6,551,838, No. 6,491,666, and No. 6,527,762, all of which are incorporated herein by reference. In one embodiment, an active actuation means is used with a hermetic reservoir cap material. Examples of suitable materials for use as a reservoir cap for covering the release opening include metals (e.g., gold, platinum, titanium), ceramics (e.g., silicon dioxide, silicon nitride, silicon carbide, diamond-like carbon, glass), or semiconductors (e.g., silicon). In one example, the reservoir cap is disintegrated by an electrothermal ablation process. In another embodiment, a passive actuation means is used that incorporates the osmotic pressure generation agent or fluid swellable material. In one type of device, a polymeric material that dissolves or degrades at a known rate (given known temperature, solvent, pH, electric field, etc.) is used to form the reservoir cap. This permits one to calculate a cap thickness to control the time at which a particular reservoir cap becomes ruptured, thereby triggering activation (i.e. permitting water transport through the semi-permeable membrane to begin). This could be tailored, for example, for use in an oral dosage form, as well as an implant.

In one embodiment, a separate semi-permeable membrane is not required with the osmotic agent. For example, if the osmotic agent is a properly cross-linked gel, then the gel can serve both as the osmotic agent and as the semi-permeable membrane.

While in typical embodiments, the water or other fluid for contacting the osmotic pressure generating agent typically comes from the fluid environment surrounding the micro-reservoir device at its site of intended operation, in an alternative embodiment, the water or fluid is obtained from a separate fluid reservoir in fluid communication with the device.

In another embodiment, a drug delivery device uses an osmotic agent to squeeze a drug formulation out of a reservoir, in contrast to pushing the drug formulation out of a reservoir. One such configuration is illustrated in FIG. 2, which shows a portion of a device 30, which includes a reservoir 34 in a substrate 32. Again, the device preferably includes tens or hundreds or more identical reservoirs in an array in the substrate. In this reservoir 34, a water-swellable polymer 38 (e.g., a cross-linked polymer, a hydrogel) is cast in place to form a tube having a central aperture in which is disposed a drug formulation 36 for release. The release end of the reservoir is sealed by reservoir cap 40, which can be formed, for example, of a sputtered metal. The end of the reservoir distal the reservoir cap, which typically would be the fill side, is sealed by a polymeric material 42 which has a hermetic overcoating 44, which also can be formed of a sputtered metal. To initiate release of the drug formulation, the reservoir cap 40 is removed, for example, by an active means such as electrothermal ablation. Water or another fluid from outside of device 30 leaks into the opened reservoir and causes the water-swellable polymer 38 to expand and displace the drug formulation 36 from the reservoir 34. In another embodiment, the water-swellable polymer is tapered such that the wall of the tube is thinnest at the reservoir release opening and thickest at the bottom of the reservoir, in order to minimize the dead space volume of the expanded gel by allowing the gel at the bottom of the reservoir to meet in the center of the reservoir. In an alternative embodiment, the device includes a water inlet aperture (which my be covered by a semi-permeable membrane) that is distal the release opening of the reservoir, so that the water swellable polymer begins swelling in the reservoir at the distal end, pushing the drug formulation towards the outlet.

In another embodiment, a collapsible container is used in place of, or possibly in addition to, the piston described above. That is, the drug formulation is protected from (i.e., separated from) the osmotic agent by a collapsible container, which typically would be formed of a polymeric or metallic material. At least one advantage in using the collapsible container is that it is compatible with tapered reservoir designs.

Figure 3:
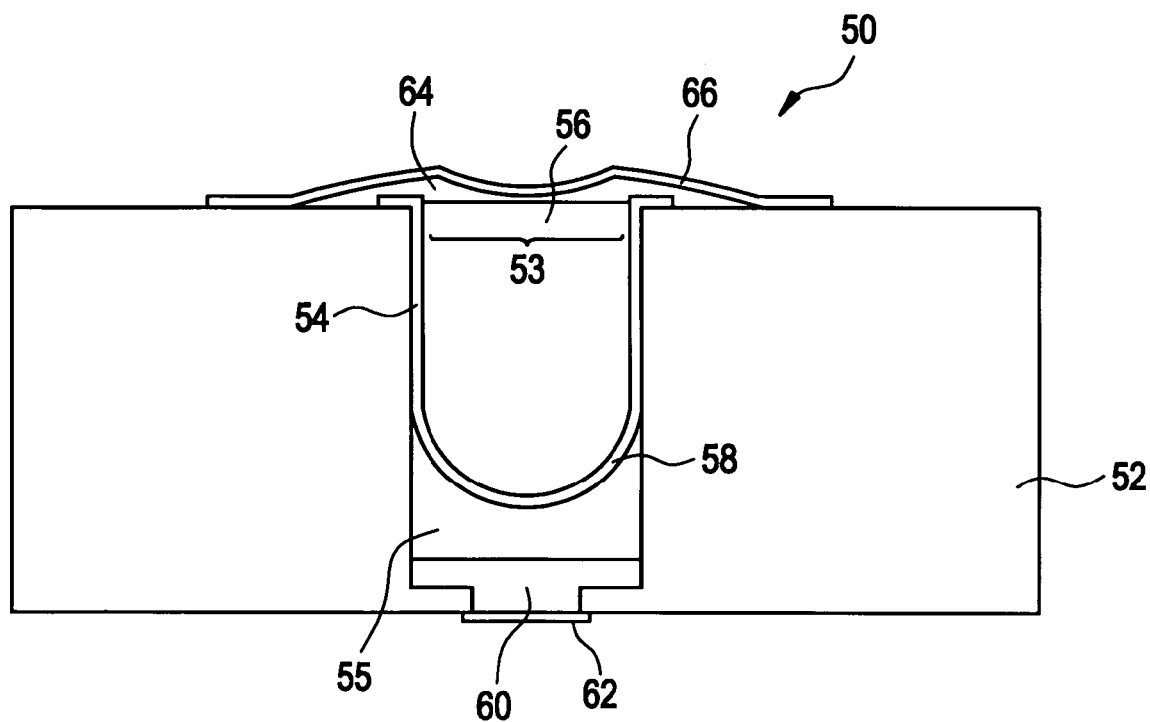
FIG. 3 is a cross-sectional view of another embodiment of a reservoir of device which uses an osmotic pressure mechanism to drive the release of molecules out of the reservoir.

One such configuration is illustrated in FIG. 3, which shows a portion of a device 50, which includes a reservoir 54 in a substrate 52. Again, the device preferably includes tens or hundreds or more identical reservoirs in an array in the substrate. The reservoir 54 contains a drug formulation 56 for release. The drug formulation is adjacent the release opening 53 and is disposed inside collapsible container 58. The collapsible container 58 separates the drug formulation 56 from an osmotic pressure generating agent 55. Another suitable swellable material, e.g., a water-swellable or other fluid-swellable material, can be used in place of the osmotic pressure generating agent. Release of the drug formulation 56 occurs when reservoir cap 62 is disintegrated to expose semi-permeable membrane 60 to water outside of the device 50. As the osmotic agent 55 swells, pressure is generated against the collapsible container, causing it to deform and push against the drug formulation 56, forcing it through the distal rupturable covering 66/64 and out of the reservoir 54. The rupturable covering is a composite hermetic seal formed of polymer layer 64 and metal layer 66.

In one embodiment, the collapsible container is created in the reservoir by depositing metal or polymer over the osmotic agent and reservoir walls. The shape of the container can be modified by the starting reservoir shape and/or the shape of the osmotic agent in the reservoir. For example, causing the osmotic agent to wet to the reservoir walls will create a rounded container. The osmotic agent may also be cast in place with a certain shape or the reservoir substrate may be micromachined to have a square pyramidal (e.g., KOH-etched Si) or other shape. The shape of the reservoir may impact how the collapsible container is made. For example, it may be difficult to deposit uniform films on steep sidewall, so a gentler sidewall angle may aid deposition uniformity. Container deposition can be performed by vacuum deposition techniques such as sputtering or evaporating, as well as other techniques such as electroplating or other techniques for thin film polymer deposition. The collapsible container typically is a biocompatible material, such as gold or platinum, or a biocompatible polymer, such as parylene. A polymer material can be deposited first and then coated with a metal for added impermeability or mechanical strength.

Figure 4:
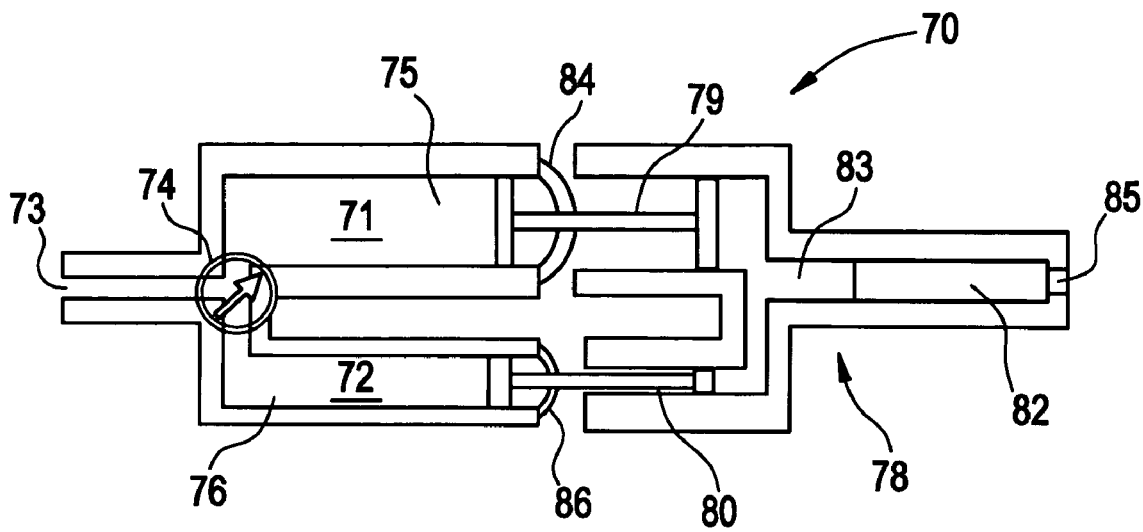
FIG. 4 is a cross-sectional view of one embodiment of a dual reservoir device which uses an osmotic pressure mechanism to drive the release of fluid molecules out of the reservoirs.

In another embodiment, the device utilizes an osmotic agent to drive a fluid drug formulation out of the device, while maintaining effective hermeticity by preventing diffusion of water and oxygen into the device. One example of such a device is illustrated in FIG. 4. In device 70, first and second fluid reservoirs 71, 72 are connected in parallel to a shared fluid switch 74 and common discharge outlet 73. The first reservoir 71 contains an inert fluid 75, and the second reservoir 72 contains a drug formulation 76. The inert fluid is substantially non-reactive with either the drug formulation or body tissues at the release site. An osmotic pump 78 is connected in parallel to both reservoirs via first and second pistons 79, 80. The osmotic pump 78 includes osmotic agent 82 in expansion space 83 and a semi-permeable membrane 85, which optionally may be covered by a reservoir cap to control initiation of water contact with the semi-permeable membrane. As the osmotic agent 82 expands, it applies pressure through the pistons 79, 80 to the inert fluid 75 and to the drug formulation 76. The fluid switch 74 can be designed to be normally closed to the second reservoir 72 and open to the first reservoir 71 for fail-safe considerations or it can be designed as a bi-stable valve for energy efficiency. The pressure created by the osmotic pump 78 therefore forces inert fluid 75 out of the first reservoir 71, though the valve 74, and out the discharge outlet 73.

When a drug dose is desired, the fluid switch 74 is actuated to open the drug reservoir 72 while closing the first reservoir 71. Water from the osmotic pump is prevented form entering the back of the reservoirs by hermetic flexible metal membranes 84, 86.

Diffusion of oxygen and water into the drug reservoir from the outlet 73 is prevented by maintaining the velocity of the fluid exiting the capillary discharge outlet above the diffusion velocity of oxygen and water. In addition, the inert fluid can be chosen to have a low solubility of oxygen and water to further isolate the drug reservoir. For example, an oil or a hydrophobic solvent could be used where low water solubility is desirable. A one-dimensional numerical simulation of the convective-diffusion equation can be performed to estimate the fluid velocity required to prevent diffusion of external species into the drug reservoir. Assuming the two fluids are completely miscible, the convective-diffusion equation in one-dimension can be written as:

$$\frac{\partial c}{\partial t} + u\frac{\partial c}{\partial x} = D\frac{\partial^2 c}{\partial x^2} \qquad \text{EQ. 1}$$

where c is the molecular species concentration, u is the fluid velocity, and D is the diffusion coefficient. The total amount of diffusing specie that is transported into the drug reservoir can be calculated by solving this equation and integrating the results in the drug reservoir section. The pressure drop across the small diffusion regulating capillary can be calculated by assuming fully developed steady laminar flow from the following equation:

$$\Delta P = \frac{32\mu u L}{d^2} \qquad \text{EQ. 2}$$

where $\mu$ is the viscosity, u is the fluid velocity, L is the capillary length, and d is the capillary diameter. Assuming the diffusion coefficient is that of water self diffusion D=2.54e-5 $cm^2/s$, a capillary and drug reservoir length of 1 cm each, and a fluid velocity of 10 $\mu m/s$, the amount of water diffusing into the drug reservoir after 1 year is on the order of $10^{-15}$ ng, and the pressure drop across the capillary is on the order of 1 Pa. The amount of inert fluid required to maintain the fluid velocity constant for 1 year is about 2.5 ml or 70 pL/sec.

In some cases it may be desirable to deliver the drug at a rate faster than that of the inert fluid in order to obtain the correct pharmacokinetic profile. Generally, the fluid volumetric delivery rate of an osmotic pump will equal the osmotic engine's output. However, relative delivery rate of the drug formulation can be accelerated by the ratio of the area of the piston in the drug reservoir section to the area of the piston in the osmotic engine section. Thus by making the area of the piston in the drug section twice as large as in the osmotic engine section, the drug volumetric delivery rate will be twice that of the osmotic engine output.

Figure 5A:
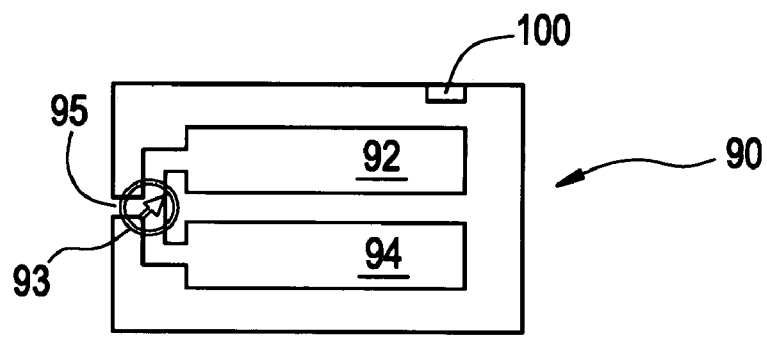
FIG. 5A is a plan cross-sectional view of one embodiment of a dual reservoir device which uses an osmotic pressure mechanism to drive the release of molecules out of the reservoir.
Figure 5B:
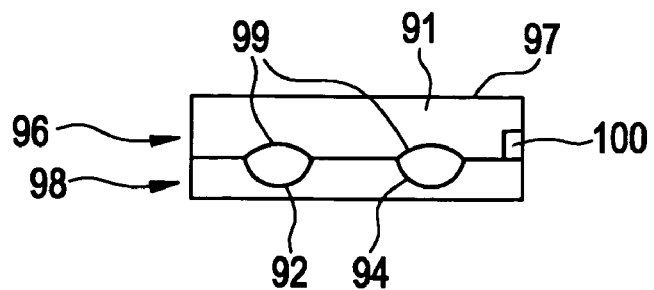
FIG. 5B is an end cross-section view of the device of FIG. 5A.

In embodiments where the volumetric delivery rate of the drug and inert fluid can be equal, the device may have a simpler design. One possible such configuration is shown in FIGS. 5A-B. Device 90 includes first and second reservoirs 92, 94 defined between an upper portion 96 comprising an osmotic agent 91 and a rigid lower portion 98. The reservoirs each have a single outlet directed to a common switch valve 93. Fluid flowing through the valve is released from discharge outlet 95. A flexible metal membrane 99 is interposed between the reservoirs 92, 94 and the upper portion 96. A rigid metal covering 97 covers all of the exterior surface of the upper portion except for a conduit area in which a semi-permeable membrane 100 is provided. As the osmotic agent draws fluid through the semi-permeable membrane 100, expanding the osmotic material, hydrostatic pressure displaces the metal membrane 99 over the particular reservoir (either 92 or 94) that is switched open, thereby forcing the fluid out of that reservoir.

In the embodiments described above, the fluid switch desirably is one having a small footprint. Suitable fluid switches include MEMs valves and small valves fabricated using other, conventional techniques, such as a traditional, but small, solenoid valve. One example is a paraffin-actuated MEMs valve, with a footprint on the order of 6 mm×6 mm, produced by Redwood MicroSystems, Inc. (Menlo Park, Calif.). Another example which may be adapted for use in these devices is a piston impregnated with magnetic media which could be switched by applying a magnetic field. The piston could be polymer photodefined in a microchannel, a technique which has been performed at Sandia National Laboratories.

Microtube Devices

In various embodiments, the micro-reservoir device for controlled release of molecules comprises an array of microtubes. As used herein, the term "microtube" refers to a metal, straight-walled structure, typically having a cylindrical opening therein. In one embodiment, the microtube has a length up to about 2 mm, and has an inner diameter of between about 0.5 and 1.0 mm.

The device further includes one of several reservoir opening techniques for releasing the molecules from the microtubes.

Advantageously, the microtube array may be made with fewer (or no) MEMs processing steps, which may reduce cost and increase yield compared to processes for making other micro-reservoir devices, may require fewer total number of joining layers, which would reduce the complexity and possible failure modes, and may simplify surface joining issues, for example, associated with hermetically sealing a microchip device. For example, it would be desirable to utilize more, or exclusively, metal-to-metal joints, for which there is a large knowledge base of techniques useful for accomplishing hermetic seals and which may lower joint stresses due to improved CTE (coefficient of thermal expansion) matching between joined surfaces. Furthermore, it would be desirable for all connections between the reservoirs and the control electronics be made in a hermetic environment, in order to reduce or eliminate the need for passivating layers and to allow the use of non-biocompatible, and potentially less expensive, electrical components in the micro-reservoir device.

Microtubes can be made in a variety of ways. For example, they can be made using a LIGA (a type of electroforming or electroplating) method. As another example, they can be made using micomaching techniques, such as drilling. In other embodiments, the microtubes could be made by rolling metal sheeting or by an extrusion process.

Figure 6B:
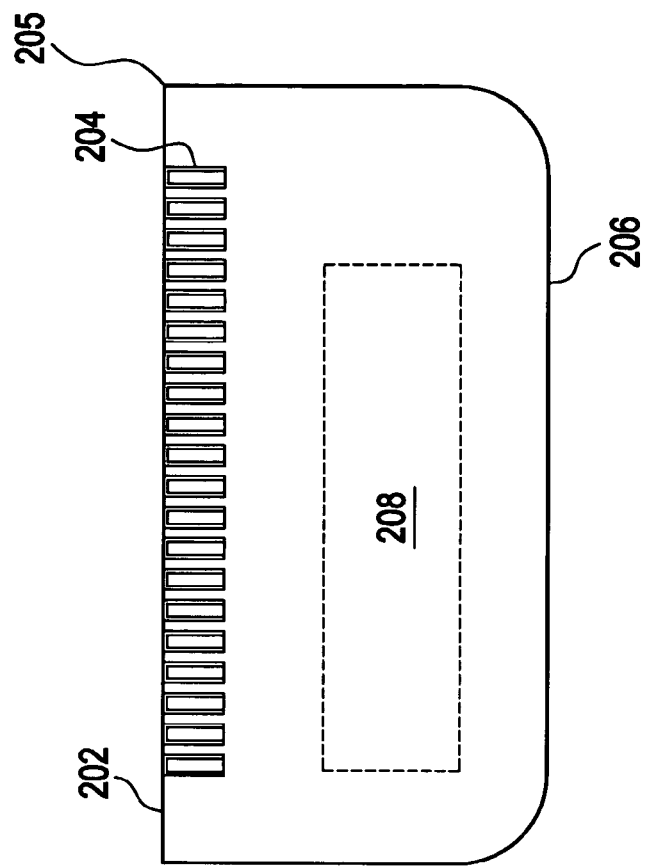
FIG. 6B is a cross-sectional view of the array in FIG. 6A as it might be packaged into a single device for controlled release of molecules.
Figure 6A:
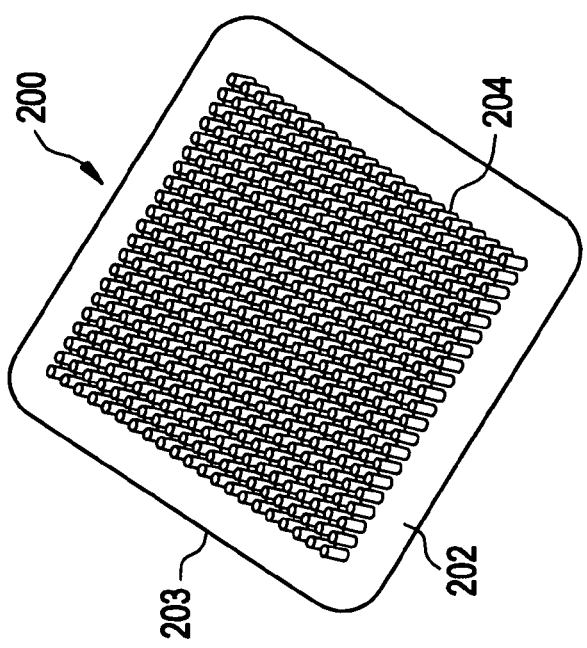
FIG. 6A is a perspective view of one embodiment of a microtube array.

One embodiment of a device comprising a microtube array is illustrated in FIGS. 6A-B. FIG. 6A shows microtube array 200 which includes base portion 202 and four hundred tubular shaped structures 204, each of which define a reservoir therein, extending from the base portion 202 in a twenty-by-twenty array. The base portion 202 and the tube structures 204 are preferably formed of a metal, for example, using a LIGA electroplating process or by brazing tubes to a metal foil in a bulk re-flow operation. Examples of suitable materials of construction for the microtube array include biocompatible metals such as titanium, gold, platinum or alloys such as Nitinol or stainless steel. The LIGA approach generally is limited to metals that can be electroplated or electroless plated. The joint between base portion 202 and the tube structures 204 preferably is hermetic. Each reservoir of the device typically is filled and sealed individually, and then, as shown in FIG. 6B, the microtube array 200 is hermetically joined to a metal can 206 (e.g., a titanium package) which can contain, for example, the control and communication electronics 208 for the device. Typically, the outer edge 203 of base portion 202 is welded to metal can 206 along its edge 205 to form a hermetic weld seam and thus a hermetically sealed device.

Figure 7:
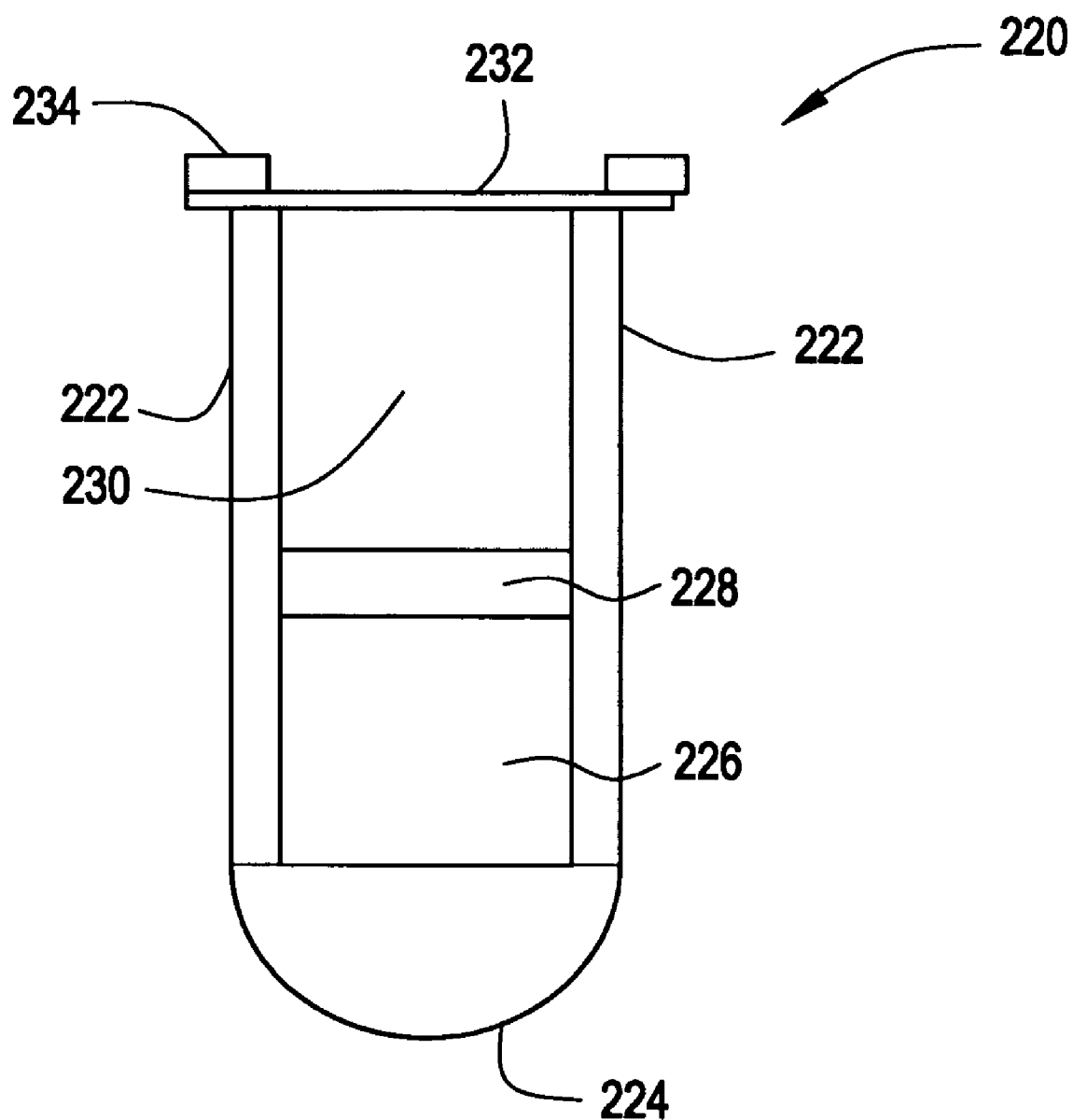
FIG. 7 is a cross-sectional view of one embodiment of a microtube reservoir comprising a drug formulation and a thermally activated expansion material to initiate release of the drug formulation.

FIG. 7 shows a cross-sectional view of one embodiment of an individual microtube 220 showing the structural details following filling and sealing. The microtube 220 includes tubular structure 222 (which are the walls defining the reservoir), rupturable covering 232, and barrier material 228, interposed between drug formulation 230 and expansion material 226. The rupturable covering 232 may further include a support layer 234 (e.g., a substrate layer that can be etched to create a membrane by exposing the bottom layer) bonded thereto in areas not intended for rupture, i.e., in areas between and joining adjacent microtubes. The support layer 234 can be a metal or ceramic structure that is used to hold the microtubes together in an array; it is thicker, stronger than the rupturable covering. The reservoir is enclosed at one end by reservoir seal 224 distal the rupturable covering 232. The device can be made and assembled as follows. First, the drug formulation 230 is loaded into the reservoir adjacent the rupturable covering 232, and then the barrier material 228 is loaded next to the drug formulation. Next, the expansion material 226 is loaded next to the barrier material 228, and the reservoir is then hermetically sealed by reservoir seal 224, e.g., by laser welding, resistance welding, or ultrasonically welding a metal sealing structure a metal sealing structure using a method that minimizes actuation of the expansion material. The entire device can be heat sunk during this operation to minimize heating effects during sealing processes.

The barrier material 228 preferably serves as a thermal barrier and/or as a diffusion barrier to prevent drug formulation 222 from diffusing into the expansion material 226. In one embodiment, the barrier material comprises one or more layers of an impermeable resilient and inert material. Examples of such materials include elastomeric polymers, e.g., acrylonitrile polymers such as acrylonitrile-butadiene-styrene terpolymer, and the like; halogenated polymers such as polytetrafluoroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; as well as elastomers in general, such as polyurethanes and polyamides, chlorinated rubbers, styrene-butadiene rubbers, and chloroprene rubbers.

The expansion material 226 preferably is one that can be thermally activated. For example, it can be activated to undergo a volumetric expansion upon heating. Non-limiting examples of expansion materials include PEG 8000 and paraffin. This expansion may take place due to a phase change or another mechanism, such as a shape change in a shape memory polymer, absorption of water by a water-absorptive polymer, etc.

Figure 8A:
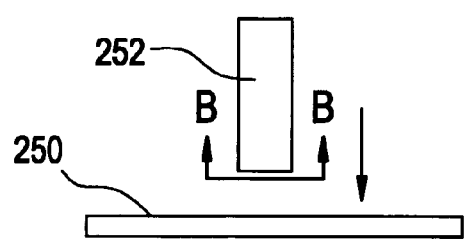
FIG. 8A is cross-sectional view of a metal foil and a defect stamp.
Figure 8B:
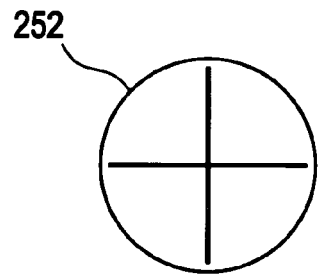
FIG. 8B is a bottom view of the defect stamp in FIG. 8A.
Figure 8C:
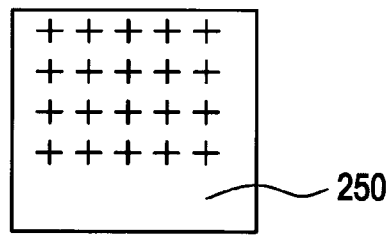
FIG. 8C is a plan view of one embodiment of a metal foil comprising an array of controlled defects.

The rupturable covering 232 ruptures to initiate release of the drug formulation from the reservoir. In one embodiment, the rupturable covering comprises or consists of a metal foil. The metal foil may be provided with one or more defects to facilitate rupture due to expansion of the expansion material. The defect can be made by a photolithography/etching defined pattern or by stamping a defect into the reservoir cap. The membrane/defect can be formed before or after filling the reservoir. FIG. 8A illustrates one embodiment of a metal foil 250 and how a defect stamp 252 could be directed to stamp a defect in the metal foil 250; FIG. 8B shows the bottom end of stamp 252; and FIG. 8C shows one embodiment of a metal foil which comprises an array of defects made therein, each of which could correspond to the rupturable covering of a single microtube.

Figure 9:
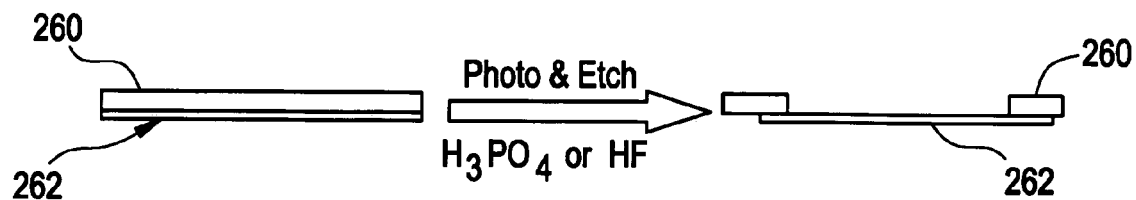
FIG. 9 is a process diagram of a method for forming a metal foil/defects for use as a rupturable covering of a microtube device.

The rupturable covering can be formed by photolithography and etching, or laser scribing. FIG. 9 illustrates one embodiment of a process, wherein a titanium seed layer 260 is provided and a thin layer of gold 262 is formed (e.g., by sputtering) on the titanium layer. Then, using a photolithography and etching process, the titanium layer is selectively removed to leave a thin gold reservoir cap layer 262 having defects therein.

In one process of forming the rupturable covering, a plasma or ion beam is used to sputter etch a portion of a gold film to create a thinner area, while protecting the titanium during the process. For example, a titanium seed layer could be patterned so that small features (e.g., bumps or lines) that are slightly raised on the surface. By planarizing the surface (e.g., by polishing or sputter etching), the gold will be thinner on top of these raised features. When the titanium is then etched away, one essentially etches 'into' the gold film by removing the raised titanium features, thus leaving a gold film with thinner areas in the pattern of the original titanium features. These thinner areas correspond with the rupturable coverings in an array.

Figure 10:
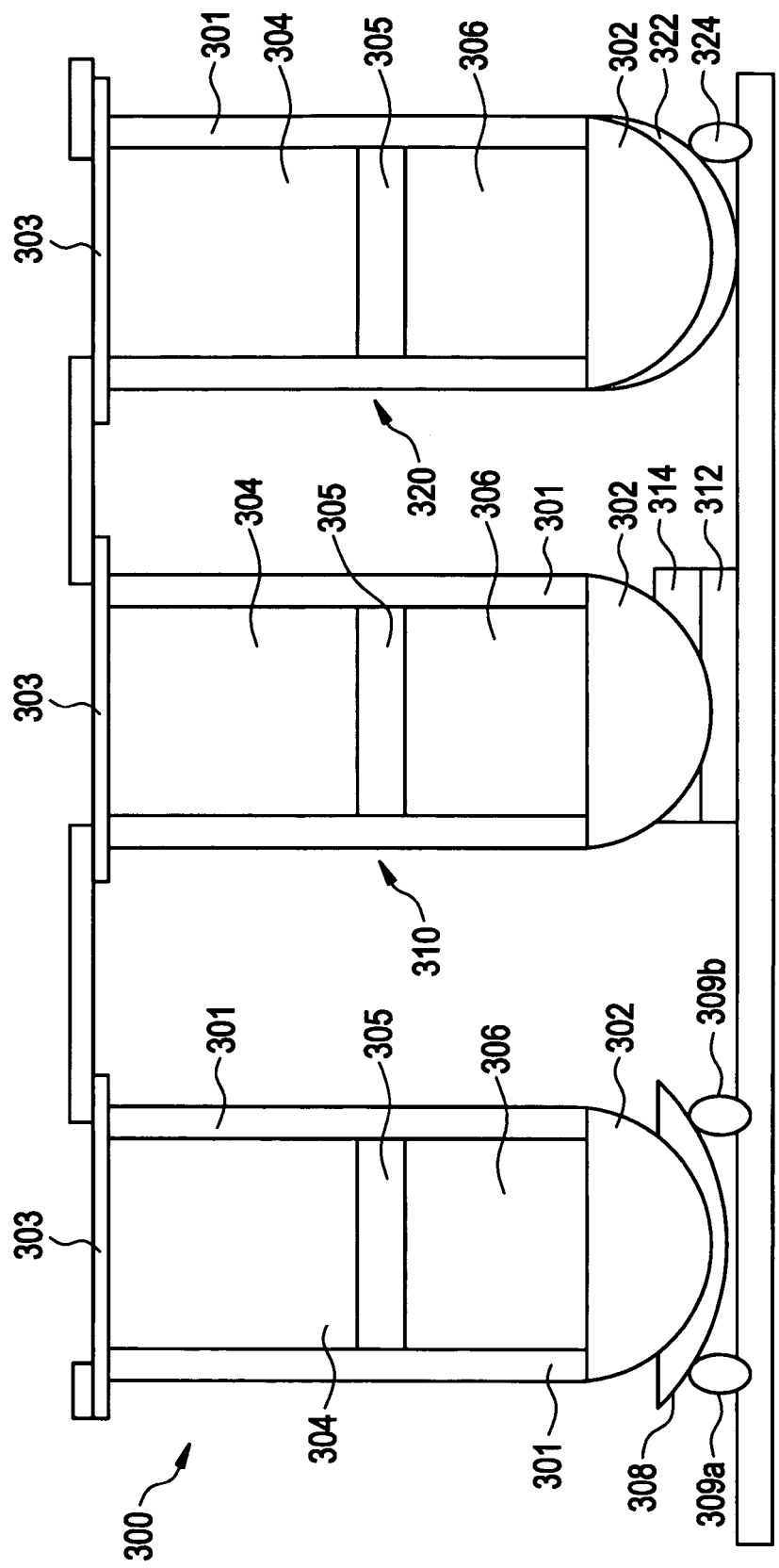
FIG. 10 is a cross-sectional view of three embodiments of microtubes each provided with a different mechanism for thermal activation to initiate release of molecules from the microtube reservoir.

FIG. 10 shows three microtubes 300, 310, and 320, each illustrates a different mechanism for applying heat to the microtube to actuate a thermally expandable material therein. Each microtube includes sidewalls 301, base end 302, rupturable covering 303, drug formulation 304, barrier material 305, and expansion material 306. Microtube 300 further includes a coating 308 which comprises a high electrical resistance material. The coating is on at least the base end 302 and enhances the heating of the expansion material when electric current is flowed through contacts 309a, 309b. Microtube 310 further includes a heating pad 312, which can comprised of a patterned thermally resistive material on a thermally insulating substrate. For example, the resistive material can be photolithographically patterned in the form of thin metal traces, a polysilicon, or a conductive polymer, and the thermally insulating substrate could be a ceramic or glass. The heating pad 312 is in thermal contact with the base end 302 via a thermally conductive interface material 314, such as a polymer or epoxy. Microtube 320 further includes an exothermic reaction coating 322 and an initiator contact 324. That is, the reaction coating is one that can selectively be made to undergo an exothermic reaction, for example, upon initiation by an electric current. One example is to use a reactive multilayer foil that undergoes an exothermic reaction when exposed to a spark. (For instance, Reactive Nanotechnologies Inc. provides a reactive multi-layer foil, which once ignited, provides enough heat to melt solder or braze without damaging the components to be joined. The use of a single foil as the heat source simplifies and speeds the joining process, while avoiding damage to heat-sensitive components. The reactive multilayer foils are fabricated by vapor depositing hundreds of nanoscale layers that alternate between elements, such as aluminum (Al) and nickel (Ni), which when exposed to a heat source, e.g., a spark, mix on an atomic scale, causing a heat reaction of over 1500° C. in less than 10 ms. Temperatures and heating rates of these reactions can be controlled by varying the composition of the foils and the thickness of the individual layers.) Such a material could be adapted as a heat source for actuation.

Figure 11:
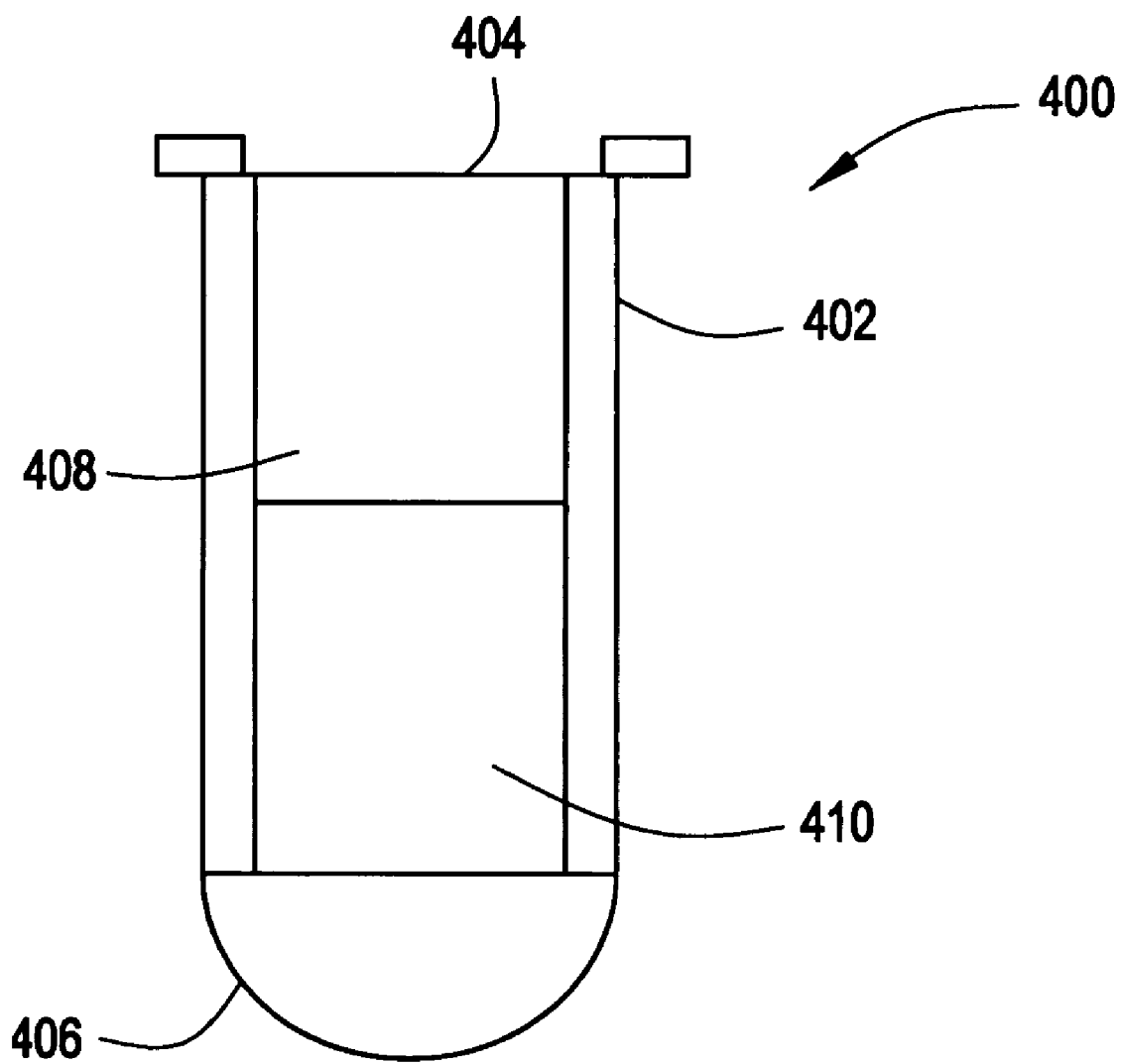
FIG. 11 is a cross-sectional view of one embodiment of a microtube formed of a shape memory alloy and using thermal activation to initiate release of molecules from the microtube reservoir.

In another embodiment, release of reservoir contents from the microtube is controlled by changing the shape of the microtube, rather than expanding a material inside the reservoir of the microtube. For example, the shape change can contract the reservoir, thereby forcing the contents of the reservoir out. In one embodiment, the microtube comprises a shape memory alloy ("SMA") known in the art, such as Nitinol. FIG. 11 shows one embodiment of a microtube which using a shape change mechanism to initiate release of reservoir contents. Microtube 400 is formed of sidewall 402, base end 406, and rupturable covering 404. The sidewall 402 is made of an SMA, and the rupturable covering is made of an SMA foil. An array of SMA reservoirs could be made, for example, by resistively welding the SMA microtubes to an SMA foil. The base end 406 also can be welded to the sidewall (i.e., the tube), for example by laser or ultrasonic welding. The microtube contains a drug formulation layer 408 adjacent the rupturable covering, and an incompressible, inert material layer 410 underneath that and adjacent the base end 406. The layer of incompressible material layer should be inert to both the drug formulation and the body of the patient. Examples of suitable incompressible, inert materials include certain polymers and gels, such as polytetrafluoroethylene or other fluoropolymers, or some polyethylene glycols. Upon heating the microtube (for example, using one of the methods described with FIG. 10), the SMA microtube undergoes a contraction that causes a hydrostatic pressure that ruptures the rupturable covering to release the drug formulation.

In some embodiments, it may be necessary or desirable to avoid the compression or compaction forces, which result from generation of pressure within the reservoir (e.g., due to osmotic pressure or expansion of an expansion material) on the drug formulation. For example, one may want a high surface area in a lyophilized formulation. In such cases, it may be desirable to provide the drug formulation within one or more rigid container sub-structures located within the microtubes. The container sub-structure would bear the mechanical pressure to rupture the rupturable covering, while keeping the drug formulation at the packaged pressure and volume. The container sub-structure could be open at one of its surfaces that faces the rupturable covering, or could be a closed structure formed of a material that dissolves or is otherwise ruptured following release, e.g., upon exposure to water or bodily fluids.

In one embodiment, the container sub-structure is made of metal using a LIGA process. In another embodiment, the container sub-structure is made of silicon by partially etching the silicon away to form the compartment and then scoring and cutting the pieces apart to yield small silicon buckets. The container sub-structure could be filled using a microinjection process, and then placed inside the microtube using a "pick and place" machine or other micromanipulator known in the art. The container sub-structure may be provided with a bio-erodible or water soluble cap that erodes/dissolves once the substructure is released into the environment.

Figure 12A:
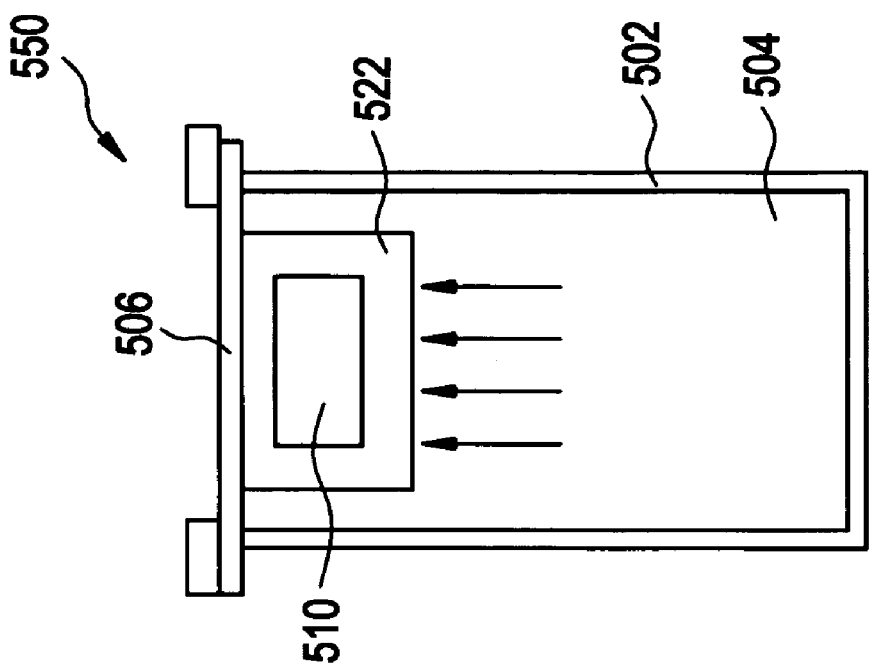
FIG. 12A is a cross-sectional view of one embodiment of a microtube loaded with a protective substructure containing drug molecules for release which is open towards the rupturable covering.
Figure 12B:
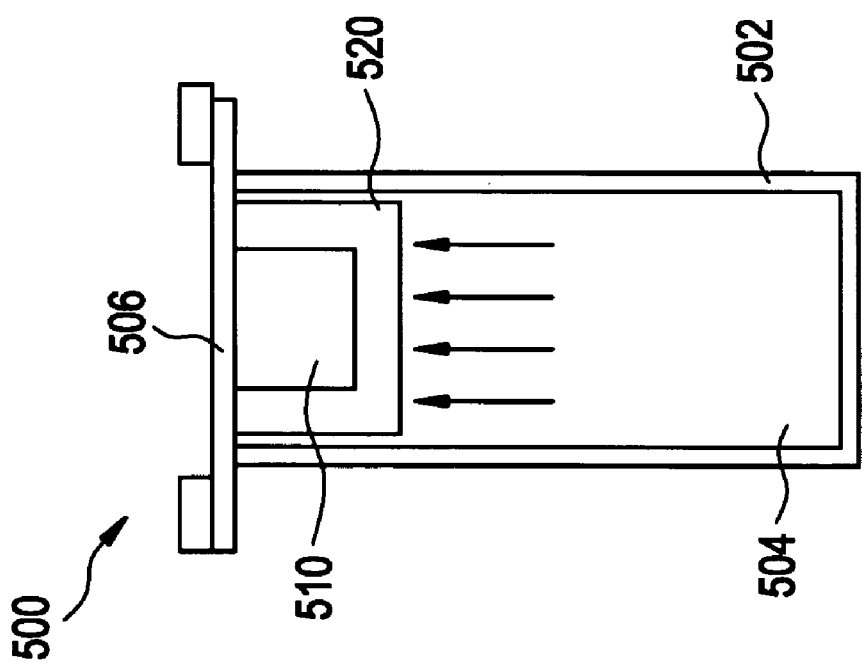
FIG. 12B is a cross-sectional view of one embodiment of a microtube loaded with a protective substructure containing drug molecules for release which is closed on all sides.

Two embodiments are shown in FIGS. 12A-B. FIG. 12A shows microtube 500 which includes a body 502 defining an interior reservoir. It further includes a rupturable covering 506. The reservoir is loaded with a thermally expandable material 504 pressing against container sub-structure 520, which contains a drug formulation 510. The sub-structure 520 is cup-shaped and has an open face that is engaged against rupturable covering 506. FIG. 12B shows another microtube 550, which is similar to microtube 500 except that the substructure 522 is different from substructure 520. The substructure 522 is enclosed and has one surface that is engaged against rupturable covering 506. Expansion of the thermally expandable material 504 can be initiated by any of a variety of mechanisms, for example, using one of the methods described with FIG. 10. In either microtube 500 or microtube 550, as enough force is applied, the rupturable covering 506 will rupture, entirely or at least partially ejecting the substructure 520/522 through the reservoir opening.

Semi-permeable Membrane

Semi-permeable compositions suitable for the semi-permeable membrane are well known in the art. Examples are disclosed in U.S. Pat. No. 4,874,388 and No. 6,270,787, which are incorporated herein by reference. Possible semi-permeable materials from which the semi-permeable membrane can be made include Hytrel polyester elastomers (DuPont), cellulose esters, cellulose ethers, and cellulose ester-ethers, water flux enhanced ethylene-vinyl acetate copolymers, semi-permeable membranes made by blending a rigid polymer with water-soluble low molecular weight compounds, and other semi-permeable materials well known in the art. Representative materials include cellulose acylate, cellulose diacylate, cellulose triacylate, cellulose acetate, cellulose diacetate, cellulose triacetate, mono-, di- and tricellulose alkanylates, mono-, di-, and tricellulose aroylates, and the like. Other materials include polyurethane, polyetherblockamide (PEBAX, commercially available from ELF ATOCHEM, Inc.), and injection-moldable thermoplastic polymers with some hydrophilicity such as ethylene vinyl alcohol. The semi-permeable membranes generally is made from semi-permeable materials having a water uptake ranging from 1% to 80%, but preferably less than 50%. The composition of the semi-permeable membrane is permeable to the passage of external liquids such as water and biological liquids. It can be substantially impermeable to the passage of drugs, osmopolymers, osmagents, and the like.

Expanding Material

A wide variety of materials known in the art may be suitable for use as the expanding material in the devices and methods described herein. In one embodiment, the expanding material is an osmotic agent, whose expansion is driven by intake of a fluid. In another embodiment, the expanding material is a thermally activated material.

The osmotic agent is a liquid-attracting agent, such as an osmagent, an osmopolymer, or a mixture of the two. Species which fall within the category of osmagent, i.e., the non-volatile species which are soluble in water and create the osmotic gradient driving the osmotic inflow of water, vary widely. Examples are well known in the art and include magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, and various monosaccharides, oligosaccharides and polysaccharides such as sucrose, glucose, lactose, fructose, and dextran, as well as mixtures of any of these various species. Species which fall within the category of osmopolymer are hydrophilic polymers that swell upon contact with water, and these vary widely as well. Osmopolymers may be of plant or animal origin, or synthetic, and examples of osmopolymers are well known in the art. Examples include poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross linked with glyoxal, formaldehyde, or glutaraldehyde and having a degree of polymerization of 200 to 30,000, a mixture of methyl cellulose, cross linked agar and carboxymethylcellulose, a mixture of hydroxypropl methylcellulose and sodium carboxymethylcellulose, polymers of N-vinyllactams, polyoxyethylene-polyoxypropylene gels, polyoxybutylene-polyethylene block copolymer gels, carob gum, polyacrylic gels, polyester gels, polyuria gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross linked indene-maleic anhydride polymers, Good-Rite polyacrylic acids having molecular weights of 80,000 to 200,000, Polyox Polyethylene oxide polymers having molecular weights of 100,000 to 5,000,000, starch graft copolymers, and Aqua-Keeps acrylate polymer polysaccharides. The osmotic agent may be a solid osmotic tablet or a fluid osmotic agent.

Examples of thermally activated expansion materials include. PEG 8000 and paraffin.

Other Device Features and Components

The positive displacement mechanisms and microtube devices described for storage and controlled release of reservoir contents can be used with or incorporated into a variety of devices, including implantable drug delivery devices, such as the microchip devices described in U.S. Pat. No. 5,797,898, No. 6,551,838, No. 6,527,762, as well as in U.S. patent application publications No. 2002/0099359 and No. 2003/0010808, which are incorporated herein by reference. The positive displacement mechanisms and devices, using osmotic pressure generating material or other swellable or expandable material, are used in combination with another device. For example, it may be part of an implantable drug delivery device that further comprises a sensor indicative of a physiological condition of a patient, an electrode for providing electrical stimulation to the body of a patient, a pump, a catheter, or a combination thereof.

Reservoirs/Substrate

The reservoirs may be located in a substrate or in a plurality of microtubes. The substrate is the structural body (e.g., part of a device) in which the reservoirs are formed, e.g., it contains the etched, machined, or molded reservoirs. A reservoir is a well, a container. MEMS methods, micromolding, and micromachining techniques known in the art can be used to fabricate the substrate/reservoirs from a variety of materials. See, for example, U.S. Pat. No. 6,123,861 and U.S. Patent Application Publication No. 2002/0107470. Examples of suitable substrate materials include metals, ceramics, semiconductors, and degradable and non-degradable polymers. The substrate, or portions thereof, may be coated, encapsulated, or otherwise contained in a biocompatible material. Examples of coating materials include poly(ethylene glycol), polytetrafluoroethylene-like materials, inert ceramics, titanium, diamond-like carbon, and the like. In one embodiment, the substrate is formed of silicon.

The substrate may consist of only one material, or may be a composite or multi-laminate material, that is, composed of several layers of the same or different substrate materials that are bonded together. The substrate can be flexible or rigid. The substrate can have a variety of shapes, or shaped surfaces. It can, for example, have a release side (i.e., an area having reservoir caps) that is planar or curved. The substrate may, for example, be in a shape selected from disks, cylinders, or spheres. In one embodiment, the release side can be shaped to conform to a curved tissue surface. In another embodiment, the back side (distal the release side) is shaped to conform to an attachment surface.

In one embodiment, the substrate is impermeable (at least during the time of use of the reservoir device) to the molecules to be delivered and to surrounding gases or fluids (e.g., water, blood, electrolytes or other solutions). In one embodiment, the substrate is biodegradable.

The substrate thickness can vary depending upon the particular device and application using the activation system described herein. For example, the thickness of a device may vary from approximately 10 μm to several centimeters (e.g., 500 μm). Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of reservoir contents needed for a particular application, although other constraints such as manufacturing limitations or total device size limitations (e.g., for implantation into a patient) also may come into play.

The substrate can have one, two, or preferably many, reservoirs. In various embodiments, tens, hundreds, or thousands of reservoirs are arrayed across the substrate. For instance, one embodiment of an implantable drug delivery device includes between 250 and 750 reservoirs, where each reservoir contains a single dose of a drug for release, which for example could be released daily over a period of several months to two years. More or less frequent dosing schedules and shorter or longer treatment durations are of course possible.

In one embodiment, the reservoir has a volume equal to or less than 500 μL (e.g., less than 250 μL, less than 100 μL, less than 50 μL, less than 25 μL, less than 10 μL, etc.) and greater than about 1 nL (e.g., greater than 5 nL, greater than 10 nL, greater than about 25 nL, greater than about 50 nL, greater than about 1 μL, etc.).

In one embodiment, the device comprises at least four or more reservoirs positioned in a two-dimensional array in a substrate or in microtubes arrayed together. For instance, the reservoirs could be arrayed in the substrate on a square matrix, with the input side of the reservoir caps electrically connected in parallel by row, and the output side of the reservoir caps electrically connected in parallel by column.

Reservoir Contents

The reservoir contents is essentially any object or material that needs to be isolated (e.g., protected from) the environment outside of the reservoir until a selected point in time, when its release or exposure is desired. In various embodiments, the reservoir contents comprises one or more types of chemical molecules for release, which optionally may be contained within a substructure.

Molecules

The reservoir contents can include essentially any natural or synthetic, organic or inorganic molecule or mixture thereof. The molecules may be in essentially any form, such as a pure solid or liquid, a gel or hydrogel, a solution, an emulsion, a slurry, or a suspension. The molecules of interest may be mixed with other materials to control or enhance the rate and/or time of release from an opened reservoir. In various embodiments, the molecules may be in the form of solid mixtures, including amorphous and crystalline mixed powders, monolithic solid mixtures, lyophilized powders, and solid interpenetrating networks. In other embodiments, the molecules are in liquid-comprising forms, such as solutions, emulsions, colloidal suspensions, slurries, or gel mixtures such as hydrogels.

The chemical molecule can be a therapeutic, prophylactic, or diagnostic agent. As used herein, the term "drug" includes any therapeutic or prophylactic agent (e.g., an active ingredient). The drug can comprise small molecules, large (i.e., macro-) molecules, or a combination thereof, having a bioactive effect. In one embodiment, the large molecule drug is a protein or a peptide. In various embodiments, the drug can be selected from amino acids, nucleic acids, oligonucleotides, polysaccharides, and synthetic organic molecules. In one embodiment, the drug is selected from nucleosides, nucleotides, and analogs and conjugates thereof. Representative examples of drugs include analgesics, anesthetics, anti-angiogenic molecules, antibiotics, antibodies, antineoplastic agents, antioxidants, antiviral agents, chemotherapeutic agents, gene delivery vectors, immunomodulators, ion channel regulators, metabolites, sugars, psychotropic agents, vaccines, vitamins. An example of a diagnostic agent is an imaging agent such as a contrast agent.

In one embodiment, the drug is a protein drug. Examples of suitable types of proteins include glycoproteins, enzymes (e.g., proteolytic enzymes), hormones (e.g., LHRH, HGH, steroids, corticosteroids), antibodies, cytokines (e.g., α-, β-, or γ-interferons), interleukins (e.g., IL-2), and insulin. In one embodiment, the drug is a bisphosphonate. In another embodiment, the drug is parathyroid hormone, such as a human parathyroid hormone, e.g., hPTH(1-84) or hPTH(1-34). In a further embodiment, the drug is a peptide with natriuretic activity, such as BNP. In another embodiment, the drug is a calcitonin. In yet another embodiment, the drug is selected from diuretics, vasodilators, inotropic agents, antiarrhythmic agents, $Ca^+$ channel blocking agents, anti-adrenergics/sympatholytics, and renin angiotensin system antagonists.

In one embodiment, the drug is a VEGF inhibitor, VEGF antibody, VEGF antibody fragment, or another anti-angiogenic agent. Examples include an aptamer, such as MACUGEN™ (Pfizer/Eyetech) (pegaptanib sodium)) or LUCENTIS™ (Genetech/Novartis) (rhuFab VEGF, or ranibizumab). These could be used in the prevention of choroidal neovascularization, which would be useful in the treatment of age-related macular degeneration or diabetic retinopathy.

In various embodiments, the drug molecules for release can be PEGylated, a technique known in the art to extend the in vivo lifetime of a bioactive molecule, for example by attaching the bioactive molecule to PEG or another oligomeric or polymeric stabilizing agent. For example, MACUGEN™ is an oligonucleotide with a molecular weight of ~50 KD, about 40 KD of which is an attached PEG molecule. The controlled release devices described herein can deliver such molecules. Advantageously, however, the controlled release devices described herein may obviate the need to PEGylate the bioactive molecule, since the bioactive molecule can be released as and when needed. That is, the devices can deliver an accurate and effective amount of drug at the desired time, avoiding the need to modify the drug (which can be costly and/or difficult to achieve) in order to keep a constant level of the bioactive molecule in the body over an extended period of time.

In one embodiment, the drug is a prostaglandin, a prostacyclin, or another drug effective in the treatment of peripheral vascular disease.

In one embodiment, a device is used to deliver a drug systemically to a patient in need thereof. In another embodiment, the construction and placement of the delivery device in a patient enables the local or regional release of drugs that may be too potent for systemic delivery of an effective dose. The reservoir contents in one reservoir or in one device can include a single drug or a combination of two or more drugs, and the reservoir contents can further include pharmaceutically acceptable carriers.

The molecules can be provided as part of a "release system," as taught in U.S. Pat. No. 5,797,898, the degradation, dissolution, or diffusion properties of which can provide a method for controlling the release rate of the molecules. The release system may include one or more pharmaceutical excipients. Suitable pharmaceutically acceptable excipients include most carriers approved for parenteral administration, including various aqueous solutions. Other excipients may be used to maintain the drug in suspensions as an aid to reservoir filling, stability, or release. Depending on the properties of the drug, such excipients may be aqueous or non-aqueous, hydrophobic or hydrophilic, polar or non-polar, protic or aprotic. See.e.g., U.S. Pat. No. 6,264,990 to Knepp et al. The release system optionally includes stabilizers, antioxidants, antimicrobials, preservatives, buffering agents, surfactants, and other additives useful for storing and releasing molecules from the reservoirs in vivo.

The release system may provide a more continuous or consistent release profile (e.g., pulsatile) or constant plasma level as needed to enhance a therapeutic effect, for example. Pulsatile release can be achieved from an individual reservoir, from a plurality of reservoirs, or a combination thereof. For example, where each reservoir provides only a single pulse, multiple pulses (i.e. pulsatile release) are achieved by temporally staggering the single pulse release from each of several reservoirs. Alternatively, multiple pulses can be achieved from a single reservoir by incorporating several layers of a release system and other materials into a single reservoir. Continuous release can be achieved by incorporating a release system that degrades, dissolves, or allows diffusion of molecules through it over an extended period. In addition, continuous release can be approximated by releasing several pulses of molecules in rapid succession ("digital" release, analogous to the digital storage and reproduction of music). The active release systems described herein can be used alone or on combination with passive release systems, for example, as described in U.S. Pat. No. 5,797,898. For example, the reservoir cap can be removed by active means to expose a passive release system, or a given substrate can include both passive and active release reservoirs.

In one embodiment, the drug formulation within a reservoir comprises layers of drug and non-drug material. As the active release mechanism ejects the reservoir contents, the multiple layers provide multiple pulses of drug release due to intervening layers of non-drug.

For in vitro applications, the molecules can be any of a wide range of molecules where the controlled release of a small (milligram to nanogram) amount of one or more molecules is required, for example, in the fields of analytic chemistry or medical diagnostics. Molecules can be effective as pH buffering agents, diagnostic reagents, and reagents in complex reactions such as the polymerase chain reaction or other nucleic acid amplification procedures. In yet other embodiments, the reservoirs contain chemical species which can be involved in a reaction, including reagents, catalysts (e.g., enzymes, metals, and zeolites), proteins, nucleic acids, polysaccharides, cells, and polymers, as well as organic or inorganic molecules which can function as a diagnostic agent. In still another embodiment, the device is adapted for use in defense applications, such as the detection of chemical or biological warfare agents.

Secondary Devices

In some embodiments, a secondary device may be provided in one or more of the reservoirs of an array that includes chemical molecules for accelerated release. Typically, such secondary devices would not be located in the same reservoir as the chemical molecules to be ejected. In one embodiment, one or more reservoirs contains a chemical or enzymatic sensor and other reservoirs contain a reagent for release to mix with the environment for detection of a reaction product by the chemical or enzymatic sensor. Release of the reagent thus would allow the secondary device to become operational.

As used herein, unless explicitly indicated otherwise, the term "secondary device" includes any device or a component thereof which can be located in a reservoir. In one embodiment, the secondary device is a sensor or sensing component thereof. As used herein, a "sensing component" includes a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Examples of biosensors that could be adapted for use in/with the reservoir devices described herein include those taught in U.S. Pat. No. 6,486,588; No. 6,475,170; and No. 6,237,398. Secondary devices are further described in U.S. Pat. No. 6,551,838.

Examples of sensing components include components utilized in measuring or analyzing the presence, absence, or change in a drug, chemical, or ionic species, energy (or light), or one or more physical properties (e.g., pH, pressure) at a site. In one embodiment, a device is provided for implantation in a patient (e.g., a human or other mammal) and the reservoir contents comprises at least one sensor indicative of a physiological condition in the patient. For example, the sensor could monitor the concentration of glucose, urea, calcium, or a hormone present in the blood, plasma, interstitial fluid, or other bodily fluid of the patient.

Several options exist for receiving and analyzing data obtained with secondary devices located within the primary device, which can be a microchip device or another device. Devices may be controlled by local microprocessors or remote control. Biosensor information may provide input to the controller to determine the time and type of activation automatically, with human intervention, or a combination thereof. For example, the operation of an implantable drug delivery system (or other controlled release/controlled reservoir exposure system) can be controlled by an on-board microprocessor (i.e., within the package of the implantable device). The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the implantable device. Power can be supplied to the implantable device locally by a battery or remotely by wireless transmission. See, e.g., U.S. Patent Application Publication No. 2002/0072784.

In one embodiment, a device is provided having reservoir contents that include drug molecules for release and a sensor/sensing component. For example, the sensor or sensing component can be located in a reservoir or can be attached to the device substrate. The sensor can operably communicate with the device, e.g., through a microprocessor, to control or modify the drug release variables, including dosage amount and frequency, time of release, effective rate of release, selection of drug or drug combination, and the like. The sensor or sensing component detects (or not) the species or property at the site of in vivo implantation and further may relay a signal to the microprocessor used for controlling release from the device. Such a signal could provide feedback on and/or finely control the release of a drug.

In one embodiment, the device contains one or more sensors for use in glucose monitoring and insulin control. Information from the sensor could be used to actively control insulin release from the same device or from a separate insulin delivery device (e.g., a conventional insulin pump).

As used herein, the term "biosensor" includes sensing devices that transduce the chemical potential of an analyte of interest into an electrical signal, as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

Reservoir Caps

In some of the osmotic pressure embodiments described herein, a reservoir cap is used to cover the semi-permeable membrane until it is desired to expose the membrane to start taking in fluid for to initiate pressure increase (and thus drug delivery). As used herein, the term "reservoir cap" includes a membrane or other structure suitable for separating the contents of a reservoir from the environment outside of the reservoir. It generally is self-supporting across the reservoir opening, although caps having additional structures to provide mechanical support to the cap can be fabricated. Selectively removing the reservoir cap or making it permeable will then "expose" the contents of the reservoir to the environment (or selected components thereof) surrounding the reservoir. In preferred embodiments, the reservoir cap is selectively disintegrated. As used herein, the term "disintegrate" is used broadly to include without limitation degrading, dissolving, rupturing, fracturing or some other form of mechanical failure, as well as a loss of structural integrity due to a chemical reaction (e.g., electrochemical degradation) or phase change (e.g., melting) in response to a change in temperature, unless a specific one of these mechanisms is indicated. In one specific embodiment, the "disintegration" is by an electrochemical activation technique, such as described in U.S. Pat. No. 5,797,898. In another specific embodiment, the "disintegration" is by an electro-thermal ablation technique, such as described in U.S. patent application Ser. No. 10/641,507, filed Aug. 15, 2003.

In active release devices, the reservoir cap generally includes any material that can be disintegrated or permeabilized in response to an applied stimulus, e.g., electric field or current, magnetic field, change in pH, or by thermal, chemical, electrochemical, or mechanical means.

In one embodiment, the reservoir cap is a thin metal film and is impermeable to the surrounding environment (e.g., body fluids or another chloride containing solution). In one variation, a particular electric potential is applied to the metal reservoir cap, which is then oxidized and disintegrated by an electrochemical reaction, to release the drug from the reservoir. Examples of suitable reservoir cap materials include gold, silver, copper, and zinc.

In another variation, the reservoir cap is heated (e.g., using resistive heating) to cause the reservoir cap to melt and be displaced from the reservoir to open it. This latter variation could be used, for example, with reservoir caps formed of a metal or a non-metal material, e.g., a polymer. In yet another variation, the reservoir cap is formed of a polymer or other material that undergoes a temperature-dependent change in permeability such that upon heating to a pre-selected temperature, the reservoir is rendered permeable to the drug and bodily fluids to permit the drug to be released from the reservoir through the reservoir cap.

In still another embodiment, the reservoir cap is formed of a conductive material, such as a metal film, through which an electrical current can be passed to electrothermally ablate it, as described in U.S. patent application Ser. No. 10/641,507, filed Aug. 15, 2003. Representative examples of suitable reservoir cap materials include gold, copper, aluminum, silver, platinum, titanium, palladium, various alloys (e.g., Au/Si, Au/Ge, Pt—Ir, Ni—Ti, Pt—Si, SS 304, SS 316), and silicon doped with an impurity to increase electrical conductivity, as known in the art. In one embodiment, the reservoir cap is in the form of a thin metal film. In one embodiment, the reservoir cap is part of a multiple layer structure, for example, the reservoir cap can be made of multiple metal layers, such as a multi-layer/laminate structure of platinum/titanium/platinum. The reservoir cap is operably (i.e. electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated (i.e., ruptured).

In passive release devices, the reservoir cap is formed from a material or mixture of materials that degrade, dissolve, or disintegrate over time, or that do not degrade, dissolve, or disintegrate, but are permeable or become permeable to molecules or energy. Representative examples of reservoir cap materials include polymeric materials, and non-polymeric materials such as porous forms of metals, semiconductors, and ceramics. Passive semiconductor reservoir cap materials include nanoporous or microporous silicon membranes.

Characteristics can be different for each reservoir cap to provide different times of release of drug formulation. For example, any combination of polymer, degree of crosslinking, or polymer thickness can be modified to obtain a specific release time or rate.

Any combination of passive and/or active release reservoir cap can be present in a single microchip device. For example, the reservoir cap can be removed by electrothermal ablation to expose a passive release system that only begins its passive release after the reservoir cap has been actively removed. Alternatively, a given device can include both passive and active release reservoirs.

Controlling Release

The device preferably is provided with a control means to control the time at which the chemical molecules are released from the device. The control means can provide intermittent or effectively continuous release. The particular features of the control means depend on the mechanism of reservoir cap activation described herein. For example, the control means can include the hardware, electrical components, and software needed to control and deliver the electric current from a power source to selected reservoir caps for actuation (i.e., opening). The control means can include an input source, a microprocessor, a timer, a demultiplexer (or multiplexer), and a power source. As used herein, the term "demultiplexer" also refers to multiplexers. The power source provides energy to activate the selected reservoir, i.e. trigger release of drug from the particular reservoir desired for a given dose. For example, the operation of the reservoir opening system can be controlled by an on-board microprocessor (e.g., the microprocessor is within an implantable or insertable device). The microprocessor can be programmed to initiate the disintegration or permeabilization of the reservoir cap in response at a pre-selected time or in response to one or more of signals or measured parameters, including receipt of a signal from another device (for example by remote control or wireless methods) or detection of a particular condition using a sensor such as a biosensor. In another embodiment, a simple state machine is used, as it typically is simpler, smaller, and/or uses less power than a microprocessor. The device can also be activated or powered using wireless means, for example, as described in U.S. 20020072784 A1 to Sheppard et al.

In one embodiment, the device includes a substrate having a two-dimensional array of reservoirs arranged therein, a release system comprising drug molecules contained in the reservoirs, anode reservoir caps covering a semi-permeable membrane for each of the reservoirs, cathodes positioned on the substrate near the anodes, and means for actively controlling disintegration of the reservoir caps. The means includes a power source and circuitry to control and deliver an electrical potential; the energy drives a reaction between selected anodes and cathodes. Upon application of a potential between the electrodes, electrons pass from the anode to the cathode through the external circuit causing the anode material (reservoir cap) to oxidize and dissolve into the surrounding fluids, exposing the release system containing the drug for delivery to the surrounding fluids, e.g., in vivo. The microprocessor directs power to specific electrode pairs through a demultiplexer as directed by a EPROM, remote control, or biosensor.

In another embodiment, the activation energy initiates a thermally driven rupturing or permeabilization process, for example, as described in U.S. Pat. No. 6,527,762. For example, the means for controlling release can actively disintegrate or permeabilize a reservoir cap using a resistive heater. The resistive heater can cause the reservoir cap to undergo a phase change or fracture, for example, as a result of thermal expansion of the reservoir cap or release system, thereby rupturing the reservoir cap and releasing the drug from the selected reservoir. The application of electric current to the resistor can be delivered and controlled using components as described above for use in the electrochemical disintegration embodiment. For example, a microprocessor can direct current to select reservoirs at desired intervals.

In yet another embodiment, control means controls electro-thermal ablation of the reservoir cap. For example, the drug delivery device could include a reservoir cap formed of an electrically conductive material, which prevents the reservoir contents from passing out from the device; an electrical input lead connected to the reservoir cap; an electrical output lead connected to the reservoir cap; and a control means to deliver an effective amount of electrical current through the reservoir cap, via the input lead and output lead, to locally heat and rupture the reservoir cap to permit water to enter the reservoir and contact the osmotic pressure generating material. In one embodiment, the reservoir cap and conductive leads are formed of the same material, where the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow, where the increase in current density through the reservoir cap causes an increase in localized heating. The reservoir cap alternatively can be formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed as described in U.S. patent application Ser. No. 10/641,507, filed Aug. 15, 2003.

Microelectronic device packages are typically made of an insulating or dielectric material such as aluminum oxide or silicon nitride. Low cost packages can also be made of plastics or reinforced epoxies (similar to those used in making printed circuit boards). Their purpose is to allow all components of the device to be placed in close proximity and to facilitate the interconnection of components to power sources and to each other, while protecting the electronics from the environment. Implanted microchip device packages will need to be hermetically sealed, e.g., in a titanium encasement, which essentially exposes only the reservoir caps.

The control means can include a microprocessor, a timer, a demultiplexer, and an input source (for example, a memory source, a signal receiver, or a biosensor), and a power source. The timer and demultiplexer circuitry can be designed and incorporated directly onto the surface of the microchip during electrode fabrication, or may be incorporated in a separate microchip. The criteria for selection of a microprocessor are small size, low power requirement, and the ability to translate the output from memory sources, signal receivers, or biosensors into an address for the direction of power through the demultiplexer to a specific reservoir on the microchip device. Selection of a source of input to the microprocessor such as memory sources, signal receivers, or biosensors depends on the microchip device's particular application and whether device operation is preprogrammed, controlled by remote means, or controlled by feedback from its environment (i.e., biofeedback).

A microprocessor is used in conjunction with a source of memory such as erasable programmable read only memory (EPROM), a timer, a demultiplexer, and a power source such as a battery or a biofuel cell. A programmed sequence of events including the time a reservoir is to be opened and the location or address of the reservoir is stored into the EPROM by the user. When the time for exposure or release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor.

Fabrication Methods

The devices and systems described herein can be made using techniques known in the art and/or described herein. Certain methods are described in U.S. Pat. No. 5,797,898; U.S. Pat. No. 6,123,861; U.S. Patent Application Publication No. 2002/0107470; and U.S. Patent Application Publication No. 2002/0151776, which are hereby incorporated by reference in their entirety. These basic device components are adapted to include the electrical leads and electrically resistive reservoir cap and the electrically induced thermal activation means described herein.

In one embodiment, soft lithography, microcontact printing, or the like is used. For example, these techniques can be useful for forming leads and reservoir caps on non-planar substrates. See, e.g., U.S. Pat. No. 6,180,239; No. 5,951,881; No, 6,355,198; and No. 6,518,168.

In one embodiment, the reservoir caps and the leads are fabricated simultaneously from the same material, that is, they are integrally formed. For example, the reservoir caps and leads can be formed using photolithography and thin film deposition techniques known in the art. Alternatively, the leads and reservoir caps can be prefabricated and then surface mounted across the reservoir opening.

In other embodiments, the reservoir caps are formed in a separate step from formation and attachment of the leads. For example, the reservoir caps could be formed onto the substrate using photolithography and thin film deposition techniques, and then, either before or after reservoir filling, the leads could be added to the substrate in electrical contact with the reservoirs. The leads could also be formed before or after reservoir cap formation, where both would be formed before device filling. This later approach may be useful to enhance drug protection, for example.

In one example, reservoir caps are formed as follows: Photoresist is patterned in the form of reservoir caps on the surface of the substrate having the reservoirs covered by the thin membrane of insulating or dielectric material. The photoresist is developed such that the area directly over the covered opening of the reservoir is left uncovered by photoresist and is in the shape of a reservoir cap. A thin film of material is deposited on the substrate by methods such as evaporation, sputtering, chemical vapor deposition, solvent casting, slip casting, contact printing, spin coating, or other thin film deposition techniques known in the art. After film deposition, the photoresist is stripped from the substrate. This removes the deposited film, except in those areas not covered by photoresist (lift-off technique). This leaves material on the surface of the substrate in the form of reservoir caps. An alternative method involves depositing the material over the entire surface of the device, patterning photoresist on top of the thin film using ultraviolet (UV) or infrared (IR) photolithography, so that the photoresist lies over the reservoirs in the shape of reservoir caps, and etching the unmasked material using plasma, ion beam, or chemical etching techniques. The photoresist is then stripped, leaving thin film caps covering the reservoirs. Typical film thicknesses of the reservoir cap material is between 0.05 μm and several microns.

In the case where the reservoir cap is the same material as the leads, the lead-reservoir cap layer is continuous and there are no connections or interfaces. In the case where the reservoir cap and the lead are of dissimilar compositions, the interface/connection is an intermetallic junction. The connections to the power source can be made by traditional IC means, flip-chip, wirebonding, soldering, and the like.

An adhesion layer may be necessary to ensure adhesion between the substrate and the reservoir cap and leads. Some examples of adhesion layers are titanium, chromium, and aluminum. Techniques for employing adhesion layers are well known in the art.

In some embodiments, insulating or dielectric materials are deposited over the reservoir cap, leads, or entire surface of the device by methods such as chemical vapor deposition (CVD), electron or ion beam evaporation, sputtering, or spin coating to protect the device or enhance biostability/biocompatibility. Examples of such materials include oxides, nitrides, carbides, diamond or diamond-like materials, or fluorocarbon films. (Some suitable materials are described in U.S. Patent Application Publication No. 2003/0080085, e.g., nanocrystalline diamond.) In one embodiment, the outer layer comprises a single layer or a multi-layer/laminate structure that includes combinations of silicon oxide ($SiO_x$), silicon nitride ($SiN_x$) or silicon carbide ($SiC_x$). In one embodiment, photoresist is patterned on top of the dielectric to protect it from etching except on the reservoir caps covering each reservoir. The dielectric material can be etched by physical or chemical etching techniques. The purpose of this film is to protect the reservoir caps and leads from corrosion, degradation, delamination, or dissolution in all areas where they do not have to be exposed to the surrounding environment, to shield electrically active components from the in vivo environment, and to enhance the biostability of the device materials.

In some embodiments, insulating materials such as silicon nitride ($SiN_x$) or silicon oxide ($SiO_x$) are deposited between the substrate and the leads by methods such as CVD, electron or ion beam evaporation, sputtering, or spin coating. The purpose of this film is to prevent electrical contact between any electrically active leads and the substrate, if the substrate is an electrical conductor. Such electrically conducting insulating layers are also deposed between layers of metal traces when they must be stacked on top of each other, for example as in devices that utilize matrix addressing of the reservoir caps.

A device incorporating the opening technology described herein can be packaged or sealed as needed for particular applications (e.g., for implantation into patients). In one embodiment, the device is hermetically sealed by welding the substrate to one or more surfaces of a packaging structure. The term "packaging structure" refers to an enclosure, casing, or other containment device for encasing the substrate, control electronics, and power elements (e.g., battery or devices for receiving wireless transmission of power), so as to expose only the release side of the substrate or reservoir caps.

Using the Systems/Devices

The controlled release/exposure devices and systems described herein can be used in a wide variety of applications. Preferred applications include the controlled delivery of a drug, biosensing, or a combination thereof. The myriad embodiments of devices that can be created to use the reservoir opening systems and methods described herein can be understood with reference to the following description.

In one embodiment, the reservoir opening devices/methods described herein are incorporated into an implantable medical device for subcutaneous drug delivery, to release drugs into the subcutaneous region which then diffuse into regional tissue or into body fluid-containing structures, including, for example, the cardiovascular system, the lymphatic system, the respiratory system, the digestive system, the central nervous system (cerebral spinal fluid), the genitourinary system, or the eyes. With the device, a drug can be administered to treat one or more of these tissues or structures or fluids within the structures, or can be transported through these tissues or structures to distal treatment locations or to cellular binding sites.

In another embodiment, the reservoir opening devices/ methods described herein are incorporated into an implantable medical device that provides direct communication between the source of the drug (e.g., a reservoir) and the particular fluid-containing structure of interest, so that when drug is released, it enters the fluid without contacting the subcutaneous region. This could be useful, for example, for administrating a drug that if released in the subcutaneous space would cause inflammation, irritation, other tissue injury/dysfunction, or would diffuse too slowly into a fluid-containing structure to achieve an effective concentration in the fluid (e.g., because of clearance mechanisms). For example, the device could directly release a therapeutic agent into one or more body cavities or tissue lumens, including an intrathecal space, an intracranial space, an abdominal/peritoneal space (e.g., for cancer therapy, endometriosis therapy), a thoracic space (e.g., for regional administration of drug in the treatment of lung cancer), an intrapericardial space (e.g., to treat mycarditis, arrythmia), a renal space, or a hepatic space. For example, the substrate could have a shape that is compatible with the fluid-containing structure, such as tubular to reside within a blood vessel (e.g., intravascular), rounded and buoyant to float in the bladder, or curved to conform to the eye. The control circuitry and power needed to activate the reservoir caps can be located in a control module outside or inside of the fluid-containing structure. If the control module is located external to the fluid-containing structure, electrical conductors can be used to connect to the reservoir caps.

In one embodiment, a medical device which includes a catheter which can be inserted into the tissue lumen or structure of interest and which has one or more drug-containing reservoirs fabricated therein, for example at a distal portion of the catheter. The body of the catheter serves as the substrate in which the reservoirs are fabricated, for example using soft lithography or other techniques known in the art. For example, tens or hundreds of micro-reservoirs could be arrayed around the catheter body at the distal tip portion. The reservoirs are hermetically sealed by conductive reservoir caps, which are electrically connected to a power source and can be disintegrated by electrothermal ablation as described herein. Advantageously, the power source and control hardware can be located at a proximal end of the catheter, so they need not fit into or be located at the delivery site. The electrical traces could be built into the catheter body or supported on an inner or outer surface of the catheter body. See U.S. Patent Application No. 2002/0111601, which disclosed one embodiment of a catheter type implantable medical device, but which utilizes a different reservoir opening technology than the electrothermal ablation system described herein.

Optionally, the catheter can have an internal fluid passageway extending between a proximal end portion and a distal end portion. The fluid passageway can be in communication with an infusion pump and a reservoir (e.g., a refillable reservoir containing a therapeutic fluid), so that the device can deliver a therapeutic fluid through the passageway to the delivery site. In one embodiment, the pump is placed abdominally in a subcutaneous pocket, and the catheter is inserted into the intrathecal space of the spine, tunneled under the skin and connected to the pump. Such an embodiment could be used, for example, in the management of chronic pain or for spasticity therapy. The microarray of drug-containing reservoirs can be provided (i) on or in the body of the catheter, (ii) in a substrate device that is located at the proximal end of the catheter and releases drug into an infusion fluid pumped across the microarray openings to form a fluid/drug mixture that is pumped through the fluid passageway of the catheter, or (iii) in a combination of these.

In one embodiment, the distal tip portion of the catheter includes one or more biological sensors to detect patient conditions that indicate the desirability or need for drug release. The sensors could extend from or be on the surface of the tip portion of the catheter body or could be located within one or more reservoirs. In one version, the device could include one catheter having a sensor on the distal end portion for implantation at a first site in vivo, and a second catheter having drug-containing reservoirs on the distal end portion for implantation at a second site in vivo. The proximal ends of the catheters would be connected with control hardware at a third site in vivo. For example, an EKG signal could be transmitted to the control module where it could be analyzed to recognize the onset of coronary ischemia. Such information could be used to justify the release of a thrombolytic agent into the venous circulation from a drug delivery system in direct communication with the venous circulation. Thrombolytic agents are currently delivered by intravenous injection because they cannot be released into the subcutaneous region. In another example, the sensor monitors the pulse in the legs or arms of the patient. Such a sensor could be used to justify the release of a vasodilator into a region, typically through an artery, to improve circulation when the pulse was attenuated. This design would be of value in treating patients with peripheral vascular disease, as these patients are not currently treated with vasodilators because no practical delivery systems are available.

In yet another embodiment, the drug-containing reservoirs are located external to the fluid-containing tissue structure. This configuration would include (i) one or more channels providing fluid communication between the reservoirs (when open) and the tissue structure, and (ii) reservoir caps to prevent body fluids from contacting the drug prior to activation. The channel may be filled with a different fluid, which is compatible with the drug, so that when the reservoir cap is activated, this fluid can facilitate release of the drug into the fluid-containing structure.

In one embodiment, a microchip device, which includes the electrothermal ablation reservoir opening device described herein, is provided for implantation into a patient, such as a human or other vertebrate animal, for controlled drug delivery, locally, regionally, or systemically. In one embodiment, the microchip device can be implanted in vivo using standard surgical or minimally-invasive implantation techniques. Such microchip devices are especially useful for drug therapies in which one needs to very precisely control the exact amount, rate, and/or time of delivery of the drug. Exemplary drug delivery applications include the delivery of potent molecules, including, hormones (e.g., PTH), steroids, cytokines, chemotherapeutics, vaccines, gene delivery vectors, natriuretic peptides, anti-VEGF aptamers, and certain analgesic agents.

In one embodiment, the drug delivery device described herein are operably connected to a pacemaker, defribrillator, hemodynamic monitor, or other biosensing device for use in cardiovascular applications, for instance.

In other embodiments, the electrothermal ablation reservoir opening device described herein is incorporated into a variety of other types and designs of implantable medical devices, such as the catheters and electrodes described in U.S. Patent Application Publication No. 2002/0111601. In another example, it could be incorporated into another medical device, in which the present devices and systems release drug into a carrier fluid that then flows to a desired site of administration, as illustrated for example in U.S. Pat. No. 6,491,666.

The devices have numerous in vivo, in vitro, and commercial diagnostic applications. The devices are capable of delivering precisely metered quantities of molecules and thus are useful for in vitro applications, such as analytical chemistry, drug discovery, and medical diagnostics, as well as biological applications such as the delivery of factors to cell cultures. In still other non-medical applications, the devices are used to control release of fragrances, dyes, or other useful chemicals. Other methods of using the devices for controlled release of molecules, as well as for controlled exposure or release of secondary devices, are described in U.S. Pat. No. 5,797,898; No. 6,123,861; No. 6,527,762; No. 6,491,666; No. 6,551,838 and U.S. Patent Application Publications No. 2002/0072784; No. 2002/0107470; No. 2002/0151776; No. 2002/0099359; and No. 2003/0010808.

Publications cited herein are incorporated by reference. Modifications and variations of the methods and devices described herein will be obvious to those skilled in the art from the foregoing detailed description. Such modifications and variations are intended to come within the scope of the appended claims.

We claim:

1. A device for the controlled release of chemical molecules comprising:

an array of discrete microtubes constructed of a metal or an alloy, each microtube comprising a reservoir defined therein;

a release formulation which comprises the chemical molecules, the release formulation being wholly contained in each reservoir;

a rupturable covering which closes an opening at a first end of each reservoir; and a means for rupturing the rupturable covering and positively displacing the release formulation through the opening at the first end, to release the chemical molecules.

2. The device of claim 1, wherein the rupturable covering is provided with one or more defects to facilitate rupture.

3. The device of claim 1, wherein the means comprises a layer of an expanding material, and the release formulation is disposed between the layer of expanding material and the rupturable covering.

4. The device of claim 3, wherein a layer of a barrier material is disposed between the release formulation and the expanding material.

5. The device of claim 3, wherein the expanding material can be activated to expand upon application of heat.

6. The device of claim 1, wherein at least a portion of the array of discrete microtubes is constructed of a shape memory alloy.

7. The device of claim 1, wherein the release formulation is contained in a rigid substructure within the reservoir.

8. The device of claim 1, wherein the release formulation is a drug formulation.

9. The device of claim 1, wherein the rupturable covering comprises a metal foil.

10. The device of claim 1, wherein the microtubes are connected by and extend from a planar base.

11. The device of claim 10, wherein the microtubes and the planar base are constructed of a biocompatible metal.

12. The device of claim 11, wherein the biocompatible metal is selected from the group consisting of titanium, gold, platinum, Nitinol, and stainless steel.

13. The device of claim 10, wherein the microtubes are fused to the planar base by an electroplating process, an electroless plating process, or by a brazing process.

14. The device of claim 10, wherein the planar base is joined to a metal package, which together enclose control electronics for controlling the means for rupturing.

15. A method for the controlled delivery of chemical molecules, comprising:

placing the device of claim 1 at a site for release of the chemical molecules; and activating the rupturing means to rupture the rupturable covering and release the chemical molecules at the site.

16. The method of claim 15, wherein the chemical molecules comprise a drug and the site is in vivo.

17. The device of claim 1, wherein each microtube has an inner diameter of between about 0.5 mm and 1.0 mm.

18. The device of claim 3, further comprising a semipermeable membrane enclosing a second end of each reservoir distal the rupturable covering, the semipermeable membrane being operable to permit selected molecules from outside the reservoir to diffuse to the expanding material to cause the expanding material to expand and displace the release formulation in an amount effective to rupture the rupturable covering and discharge the release formulation from the reservoir.

19. The device of claim 18, further comprising a reservoir cap, which covers the semi-permeable membrane, and a means for selectively disintegrating the reservoir cap.

20. The device of claim 5, wherein the means for rupturing comprises a reactive coating over at least a portion of the end of the microtube distal the rupturable covering.

21. A device for the controlled release of chemical molecules comprising:

an array of discrete microtubes, each microtube comprising a reservoir defined therein;

a release formulation which comprises the chemical molecules, the release formulation being disposed in each reservoir;

a rupturable covering enclosing a first end of each reservoir; and a means for rupturing the rupturable covering and positively displacing the release formulation through an opening at the first end, to release the chemical molecules, wherein the means for rupturing comprises a layer of an expanding material which can be activated to expand upon application of heat and a resistive heating element or resistive coating for heating the end of the microtube distal the rupturable covering upon application of an electric current through the resistive heating element or resistive coating, the release formulation being disposed between the layer of expanding material and the rupturable covering.

22. The device of claim 21, wherein the release formulation is a drug formulation.

23. The device of claim 21, wherein the rupturable covering comprises a metal foil.

24. The device of claim 21, wherein the rupturable covering is provided with one or more defects to facilitate rupture.

25. The device of claim 21, wherein the microtubes are constructed of titanium, gold, platinum, Nitinol, stainless steel, or another metal or alloy.

26. The device of claim 21, wherein the microtubes are connected by and extend from a planar base.

27. The device of claim 26, wherein the planar base is joined to a metal package, which together enclose control electronics for controlling the means for rupturing.

* * * * *